US008058515B2

(12) United States Patent
Gaxiola et al.

(10) Patent No.: US 8,058,515 B2
(45) Date of Patent: *Nov. 15, 2011

(54) PLANT CELLS AND PLANTS OVEREXPRESSING VACUOLAR PROTON PYROPHOSPHATASES

(75) Inventors: Roberto A. Gaxiola, Mansfield Center, CT (US); Seth L. Alper, Boston, MA (US); Gerald R. Fink, Chestnut Hill, MA (US)

(73) Assignees: University of Connecticut, Farmington, CT (US); Beth Israel Deaconess Medical Center, Boston, MA (US); Whitehead Institute for Biomedical Research, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/119,683

(22) Filed: May 2, 2005

(65) Prior Publication Data

US 2005/0262598 A1 Nov. 24, 2005

Related U.S. Application Data

(63) Continuation of application No. 09/834,998, filed on Apr. 13, 2001, now abandoned, which is a continuation of application No. 09/644,039, filed on Aug. 22, 2000, now abandoned.

(60) Provisional application No. 60/164,808, filed on Nov. 10, 1999.

(51) Int. Cl.
*A01H 5/00* (2006.01)
*C12N 15/82* (2006.01)
*C12N 5/04* (2006.01)

(52) U.S. Cl. ........ 800/295; 800/298; 800/278; 800/289; 800/290; 435/419; 435/468

(58) Field of Classification Search .................. None
See application file for complete search history.

(56) References Cited

U.S. PATENT DOCUMENTS

| | | | |
|---|---|---|---|
| 4,707,359 A | 11/1987 | McMullen | |
| 4,945,050 A | 7/1990 | Sanford | |
| 5,071,962 A | 12/1991 | Morrison | |
| 5,100,792 A | 3/1992 | Sanford | |
| 5,294,593 A | 3/1994 | Kahn | |
| 5,310,673 A | 5/1994 | Shibata | |
| 5,451,240 A | 9/1995 | Trowbridge | |
| 5,538,877 A | 7/1996 | Lundquist et al. | |
| 5,750,862 A | 5/1998 | John | |
| 5,837,545 A | 11/1998 | Guy et al. | |
| 5,859,338 A | 1/1999 | Meyerowitz | |
| 5,977,441 A | 11/1999 | Oliver | |
| 6,063,731 A | 5/2000 | Back | |
| 6,069,009 A | 5/2000 | Pepin | |
| 6,087,175 A | 7/2000 | John | |
| 6,087,176 A | 7/2000 | Durzan | |
| 6,198,026 B1 | 3/2001 | Fabijanski | |
| 6,200,808 B1 | 3/2001 | Simmonds | |
| 6,239,327 B1 | 5/2001 | Grossniklaus | |
| 6,248,935 B1 | 6/2001 | Cigan | |
| 6,255,564 B1 | 7/2001 | Fabijanski | |
| 6,936,750 B2 * | 8/2005 | Blumwald et al. | 800/298 |
| RE39,114 E | 5/2006 | Barry | |
| 7,041,875 B1 | 5/2006 | Blumwald | |
| 7,071,378 B1 | 7/2006 | Bonello | |
| 7,071,382 B2 | 7/2006 | Cahoon | |
| 7,534,933 B2 | 5/2009 | Gaxiola | |
| 2002/0023282 A1 | 2/2002 | Gaxiola | |
| 2002/0178464 A1 | 11/2002 | Gaxiola et al. | |
| 2003/0213015 A1 | 11/2003 | Gaxiola | |
| 2005/0278808 A1 | 12/2005 | Gaxiola | |
| 2008/0104733 A1 | 5/2008 | Gaxiola et al. | |
| 2009/0288222 A1 | 11/2009 | Gaxiola et al. | |

FOREIGN PATENT DOCUMENTS

| | | |
|---|---|---|
| WO | WO 97/26365 | 7/1997 |
| WO | WO 99/05902 | 2/1999 |
| WO | WO 99/47679 | 9/1999 |
| WO | WO 99/61616 | 12/1999 |
| WO | WO 00/75330 | 12/2000 |
| WO | WO 01/33945 | 5/2001 |
| WO | WO 01/45494 A2 | 6/2001 |
| WO | WO 02/15674 | 2/2002 |
| WO | WO 02/16558 | 2/2002 |
| WO | WO 02/072849 A2 | 9/2002 |
| WO | WO 2007/049275 A2 | 5/2007 |
| WO | WO 2007/053974 A1 | 5/2007 |
| WO | WO 2009/020528 A1 | 2/2009 |

OTHER PUBLICATIONS

Kim et al. (Plant Physiol., 106:375-382).*
Maeshima (Biochimica et Biophysica Acta 1465:37-51, 2000).*
Gaxiola et al. (PNAS, 96:1480-1485, Published Feb. 16, 1999).*
Kay et al. (Science, 236:1299-1302, 1987).*
Bremberger et al. (Planta, 175:465-470, 1988).*
Nakamura et al. (Plant Cell Physiol., 33:139-149, 1992).*
Rausch et al. (J. Plant Physiol. 148:425-433, 1996).*
Barkla et al. (Annu. Rev. Plant Physiol. Plant Mol. Biol., 47:159-184, 1996).*
Kay et al (Science, 236:1299-1302, 1987).*
Apse, M.P., et al., "Salt Tolerance Conferred by Overexpression of a Vacuolar Na+/H+ Antiport in *Arabidopsis*," *Science* 285: 1256-1258 (Aug. 20, 1999).

(Continued)

*Primary Examiner* — Vinod Kumar
(74) *Attorney, Agent, or Firm* — Hamilton, Brook, Smith & Reynolds, P.C.

(57) ABSTRACT

The present invention relates to a transgenic plant, comprising one or more plant cells transformed with exogenous nucleic acid which increases expression of vacuolar pyrophosphatase in the plant. Also encompassed by the present invention are transgenic progeny and seeds of the transgenic plants described herein. Progeny transgenic plants grown from seed are also described. Plant cells (e.g., root cells, stem cells, leaf cells) comprising exogenous nucleic acid which increases expression of vacuolar pyrophosphatase in the plant cells are also the subject of the present invention. Also encompassed by the present invention are methods of making a transgenic plant described herein. The present invention also relates to a method of increasing the yield of a plant, a method of making a plant which is larger than its corresponding wild type plant, and a method of producing a transgenic plant with increased salt tolerance.

34 Claims, 4 Drawing Sheets

OTHER PUBLICATIONS

Gaxiola, R., et al., "A Novel and Conserved Salt-Induced Protein is an Important Determinant of Salt Tolerance in Yeast," *EMBO J.* 11(9):3157-3164 (Sep. 1992).

Gaxiola, R.A., et al., "The Yeast CLC Chloride Channel Functions in Cation Homeostasis," *Proc. Natl. Acad. Sci. USA* 95(7):4046-4050 (Mar. 1998).

Gaxiola, R.A., et al., "The *Arabidosis thaliana* Proton Transporters, AtNhx1 and Avpl, Can Function in Cation Detoxification in Yeast," *Proc. Natl. Acad. Sci. USA* 96:1480-1485 (Feb. 1999).

Hechenberger, M., et al., "A Family of Putative Chloride Channels from *Arabidopsis* and Functional Complementation of a Yeast with a CLC Gene Disruption," *J. Biol. Chem.* 271(52):33632-33638 (Dec. 27, 1996).

Nass, R., et al., "Novel Localization of a Na+/H+ Exchanger in a Late Endosomal Compartment of Yeast," *J. Biol. Chem.* 273(33):21054-21060 (Aug. 14, 1998).

Sato, M.H., et al., "The *AtVAM3* Encodes a Syntaxin-Related Molecule Implicated in the Vacuolar Assembly in *Arabidopsis thaliana*," *J. Biol. Chem.* 272(39):24530-24535 (Sep. 26, 1997).

Stitt, M., "Pyrophosphate as an Energy Donor in the Cytosol of Plant Cells: an Enigmatic Alternative to ATP," *Bot. Acta* 111:167-175 (1998).

Xie, X.S., et al., "Isolation and Reconstruction of the Chloride Transporter of Clathrin-Coated Vesicles," *J. Biol. Chem.* 264(32):18870-18873 (Nov. 1989).

Topfer, R., et al., "A Set of Plant Expression Vectors for Transcriptional and Translational Fusions," *Nucleic Acid Res.* 15(14):5890 (Jul. 24, 1987).

Zhen, R.G., et al., "Acidic Residues Necessary for Pyrophosphate—Energized Pumping and Inhibition of the Vacuolar H+-pyrophosphatase by N,N'-Dicyclohexylcarbodiimide," *J. Biol. Chem.* 272(35):22340-22348 (Aug. 29, 1997).

Ballesteros, E., et al., "Na+/H+ antiport activity in tonoplast vesicles isolated from sunflower roots induced by NaCl stress," *Physiol. Plant.*, 99:328-334 (1997).

Gibeaut, D.M., et al., "Maximal Biomass of *Arabidopsis thaliana* Using a Simple, Low-Maintenance Hydroponic Method and Favorable Environmental Conditions," *Plant Physiol.* 115:317-319 (1997).

Kim, Y., et al., "Isolation and Characterization of cDNAs Encoding the Vacuolar H+-Pyrophosphatase of *Beta vulgaris*," *Plant Physiol.*, 106:375-382 (1994).

Kisch, M., et al., "Salt stress induces an increased expression of V-type H+-ATPase in mature sugar beet leaves," *Plant Mol. Biol.*, 32:543-547 (1996).

Neuhaus, J-M, and Rogers, J.C., "Sorting of proteins to vacuoles in plant cells," *Plant Mol. Biol.*, 38:127-144 (1998).

Paris, N., et al., "Molecular Cloning and Further Characterization of a Probable Plant Vacuolar Sorting Receptor," *Plant Physiol.*, 115:29-39 (1997).

Serrano, R., and Gaxiola, R., "Microbial Models and Salt Stress Tolerance in Plants," *Critical Reviews in Plant Sciences*, 13(2):121-138 (1994).

Tsiantis, M.S., et al., "Salt regulation of transcript levels for the c subunit of a leaf vacuolar H+-ATPase in the halphyte *Mesembryanthemum crystallinum*," *The Plant Journal*, 9(5):729-736 (1996).

Vitale, A., and Raikhel, N.V., "What do proteins need to reach different vacuoles?," *Trends in Plant Science*, 4:148-154 (1999).

Zhen, R.G., et al., "Acidic Residues Necessary for Pyrophosphate-energized Pumping and Inhibition of the Vacuolar H+-pyrophosphatase by N,N'-Dicyclohexylcarbodiimide," *J. of Biol. Chem.*, 272(35):22340-22348 (1997).

Safafian, V., et al., "Molecular cloning and sequence of cDNA encoding the pyrophosphate-energized vacuolar membrane proton pump of *Arabidopsis thaliana*," *Proc. Natl. Acad. Sci. USA*, 89:1775-1779 (1992).

Lerchl, J., et al., "Molecular cloning, characterization and expression analysis of isoforms encoding tonoplast-bound proton-translocating inorganic pyrophosphatase in tobacco," *Plant Mol. Biol.*, 29:833-840 (1995).

Kim, E.J., et al., "Heterologous expression of plant vacuolar pyrophosphatase in yeast demonstrates sufficiency of the substrate-binding subunit for proton transport," *Proc. Natl. Acad. Sci. USA*, 91:6128-6132 (1994).

Schwappach, B., et al., "Golgi Localization and Functionally Important Domains in the $NH_2$, and COOH Terminus of the Yeast CLC Putative Chloride Channel Geflp," *J. of Biol. Chem.*, 273(24):15110-15118 (1996).

Hong, B., et al., "Identification of a Calmodulin-Regulated $Ca^{2+}$-ATPase in Endoplasmic Reticulm," *Plant Physiology*, 119:1165-1175 (1999).

Burbidge, A., et al., "Structure and expression of a cDNA encoding a putative neoxanthin cleavage enzyme (NCE), isolated from a wilt-related tomato (*Lycopersicon esculentum Mill.*) Library," *J. of Exp. Botany*, 47(317):2111-2112 (1997).

Al-Awqati, Q., "Chloride channels of intracellular organelles," *Current Opinion in Cell Biology* 1995, 7:504-508.

Antebi, A. and Fink, G. R., "The Yeast $Ca^{2+}$-ATPase Homologue, PMRI, is Required for Normal Golgi Function and Localizes in a Novel Golgi-Like Distribution," *Mol. Biol. Cell*, 3:633-654, (1992).

Ballester, R., et al., "Genetic Analysis of Mammalian GAP Expressed in Yeast," *Cell*, 59:681-686, (1989).

Baltscheffsky, M., et al., "$H^+$-Proton-Pumping Inorganic Pyrophosphatase: A Tightly Membrane-Bound Family," *FEBS Letters*, 452:121-127, (1999).

Barkla, B.J., et at, "The Plant Vacuolar $Na^+/H^+$ Antiport," *Symp. Soc. Exp. Biol.*, 48:141-153, (1994).

Barkla, B.J., et al., "Tonoplast $Na^+/H^+$ Antiport Activity and Its Energization by the Vacuolar $H^+$-ATPase in the Halophytic Plant *Mesembryanthemum crystallinum* $L^1$," *Plant Physiol.*, 109:549-556, (1995).

Bassham, D.C. and Raikhel, N.V., "An Arabidopsis VPS45p Homolog Implicated in Protein Transport to the Vacuole," *Plant Physiol.*, 117:407-415, (1998).

Bechtold, N., et al., "In Planta Agrobacterium Mediated Gene Transfer by Infiltration of Adult *Arabidopsis* Plants," *C.R. Jances Acad. Sci. Ser. III Sci. Vie*, 361:1 194-1199, (1993).

Becker, D., "Bynary Vectors Which Allow the Exchange of Plant Selectable Markers and Reporter Genes," *Nucleic Acids Research*, 18: pp. 203, (1990).

Bidonde, S., et al., "Expression and Characterization of Three Tomato I-Aminocyclopropane-I-Carboxylate Oxidase cDNA in Yeast," *Eur. J. Biochem.*, 253:20-26, (1998).

Carystinos, G.D., et al. "Vacuolar $H^+$-Translocating Pyrophosphatase Is Induced by Anoxia or Chilling in Seedlings of Rice[1]," *Plant Physiol.*, 108:641-649, (1995).

Counillon, L., et al., "A Point Mutation of the $Na^+/H^+$Exchanger Gene (NHE1) and Amplification of the Mutated Allele confer Amiloride Resistance Upon Chronic Acidosis," *Proc. Natl. Acad. Sci. USA*, 90:4508-4512, (1993).

Cunningham, S.D., and Ow., D.W., "Promises and Prospects of Phytoremediation," *Plant Physiol.*, 110:715-719, (1996).

Darley, C.P., et al., "Chill-Induced Changes in the Activity and Abundance of the Vacuolar Proton-Pumping Pyrophosphatase From Mung Bean Hypocotyls," *Plant Physiol.*, 109:659-665, (1995).

Davies, J.M., "The Bioenergetics of Vacuolar H+ Pumps," In: Leigh RA, Sanders D (eds) The Plant Vacuole, pp. 340-363. Academic Press, San Diego, (1997).

Davies, J. M., "Vacuolar Energization: Pumps, Shunts and Stress," *Journal of Experimental Botany*, 48(308):633-641, (1997).

Drews, G., et at, "In Situ Hybridization to RNA in Plant Tissue," *Plant Molec. Biol. Rep.*, 5:242-250, (1988).

Drozdowicz, Y.M., et al., "AVP2, a Sequence-Divergent, $K^+$-Insensitive $H^+$-Translocating Inorganic Pyrophosphatase from *Arabidopsis*," *Plant Physiol.*, 123:353-362, (2000).

Farré, E. M., et al., "Accceleration of Potato Tuber Sprouting by the Expression of a Bacterial Pyrophosphatase," *Nature Biotechnology*, 19: 268-272 (2001).

Galway, et al., "Growth and Ultrastructure of *Arabidopsis* Root Hairs: The rhd3 Mutation Alters Vacuole Enlargement and Tip Growth," *Planta*, 201:209-218, (1997).

Gaxiola, et al., "Drought-and-Salt-Tolerant Plants result From Overexpression of the AVP1 $H^+$-Pump," *PNAS*, 98(20):11444-11449, (2001).

Gietz, D., et al., "Improved Method for High Efficiency Transformation of Intact Yeast Cells," *Nucl. Acids Res.*, 20:p. 1425, (1992).

Gogarten, et al. "The Use of Antisence mRNA to Inhibit the Tonoplast $H^+$ ATPase in Carrot," *The Plant Cell*, 4:851-864, (1992).

Guiltinan, M.J. and McHenry, L., "Epitope Tagging for the Detection of Fusion Protein Expression in Transfenic Plants," *Methods Cell Biol.*, 49:143-151, (1995).

Guo, H.H., et al., "Protein Tolerance to Random Amino Acid Change," *PNAS*, 101(25):9205-9210, (2004).

Gupta, et al. "Maintenance of Photosynthesis at Low Leaf Water Potential in Wheat,", *Plant Physiol.*, 89:1358-1365, (1989).

Hajdukiewicz, Z., et al. "The Small, Versatile *pPZP* Family of *Agrobacterium* Binary Vectors for Plant Transformation," *Plant Molecular biology*, 25:989-994, (1994).

Haughn, G.W. and Somerville, C., "Sulfonylurea-resistant Mutants of *Arabidopsis thaliana*," *Mol Gen Genet*, 204: 430-434 (1986).

Hill, M.A. and Preiss J., "Functional Analysis of Conserved Histidines in ADP-Glucose Pyrophosphorylase from *Escherichia coli*," *Biochemical and Biophysical Research Communications*, 244:573-577, (1998).

Hirschi, et al., "CAxl, an $H^+/Ca^{2+}$ Antiport From *Arabidopsis*," *Proc. Natl. Acad. Sci. USA*, 93:8782-8786, (1996).

Jauh, G.Y., et al., "Tonoplast Intrinsic Protein Isoforms as Markers for Vacuolar Functions," *The Plant Cell*, 11:1867-1882, (1999).

Kennedy, B.K., et al., "Redistribution of Silencing Proteins From Telomeres to the Nucleolus Is Associated With Extension of Life Span in *S. cerevisiae*," *Cell*, 89:381-391, (1997).

Kieber, J.J., et al., "CTR1, a Negative Regulator of the Ethylene Response Pathway in *Arabidopsis*, Encodes a Member of the Rat Family of Protein Kinases," *Cell*, 72:427-441, (1993).

Krysan, P.J., et al., "Identification of Transferred DNA Insertions Within *Arabidopsis* Genes Involved in Signal Transduction and Ion Transport," *Proc. Natl. Acad. Sci. USA*, 93:8145-8150, (1996).

Lazar, E., et al., "Transforming Growth Factor α: Mutation of Aspartic Acid 47 and Leucine 48 Results in Different Biological Activities," *Molecular and Cellular Biology*, 8(3):1247-1252, (1988).

Leigh, "Solute Composition of Vacuoles," *Advances in Botanical Research, The Plant Vacuole*, 25:171-194, (1997).

Levi, M., et al., "Rapid Immunofluorescent Determination of Cells in the S Phase in Pea Root Meristems: An Alternative to Autoradiography," *Physiologic Plantarum*, 71: 68-72, (1987).

Li, J., et al., "*Arabidopsis* $H^+$-PPase AVP1 Regulates Auxin-Mediated Organ Development," *Science*, 310:121-125, (2005).

Madhani, H.D., et al., "MAP Kinases with Distinct Inhibitory Functions Impart Signaling Specificity During Yeast Differentiation," *Cell*, 91:673-684, (1997).

Madrid, R., et al., "Ectopic Potassium Uptake in trk1 trk2 Mutants of *Saccharomyces cerevisiae* Correlates With a Highly Hyperpolarized Membrane Potential," *The Journal of Biological Chemistry*, 272(24):14838-14844, (1998).

Marty, F., "The Biogenesis of Vacuoles: Insights from Microscopy," In: Leight RA, Sanders D (eds) The Plant Vacuole, pp. 1-42. Academic Press, San Diego, (1997).

McCormick, S., "Transformation of tomato with *Agrobacterium tumerfaciens*," In: Lindsey, K. (ed) Plant Tissue Culture Manual, pp. 1-9. Kluwer Academic Publishers, Dordrecht, The Netherlands, (1991).

McCusker, J.H. et al., "Pleiotropic Plasma Membrane ATPase Mutations of *Saccharomyces cerevisiae*," *Molecular and Cellular Biology*, 7(11):4082-4088, (1987).

Mitsuda, N., et al., "Pollen-Specific Regulation of Vacuolar $H^+$-PPase Expression by Multiple cis-Acting Elements," *Plant Molecular Biology*, 46: 185-192 (2001).

Mullen, R.T., et al., "Identification of the Peroxisomal Targeting Signal for Cottonseed Catalase," *The Plant Journal*, 12(2):313-322, (1997).

Murguia, J.R., et al., "A Salt-Sensitive 3'('),5'-Bisphosphate Nucleotidase Involved in Sulfate Activation," *Science*, 267:232-234, (1995).

Nass, R., et al., "Intracellular Sequestration of Sodium by a Novel $Na^+/H^+$ Exchanger in Yeast Is Enhanced by Mutations in the Plasma Membrane $H^+$-ATPase," *The Journal of Biological Chemistry*, 272(42):26145-26152, (1997).

Niyogi, K.K. and Fink, G.R., "Two Anthranilate Synthase Genes in *Arabidopsis*: Defense-Related Regulation of the Tryptophan Pathway," *The Plant Cell*, 4:721-733, (1992).

Park, S., et al., "Up-Regulation of a $H^+$-Pyrophosphatase ($H^+$-PPase) as a Strategy to Engineer Drought-Resistant Crop Plants," *PNAS* 102 (52): 18830-18835 (2005).

Quesada, A., et al., "PCR-Identification of a *Nicotiana plymbaginifolia* cDNA Homologous to the High-Affinity Nitrate Transporters of the crnA Family," *Plant Molecular Biology*, 34:265-274, (1997).

Randall, S.K. and Sze, H., "Properties of the Partially Purified Tonoplast $H^+$-Pumping ATPase From Oat Roots," *The Journal of Biological Chemistry*, 261(3):1364-1371, (1986).

Rate, D.N., et al., "The Gain-of-Function *Arabidopsis* acd6 Mutant Reveals Novel Regulation and Function of the Salicylic Acid Signaling Pathway in Controlling Cell Death, Defenses, and Cell Growth," *The Plant Cell*, 11:1695-1708, (1999).

Rausch, et al., Salt Stress Responses of Higher Plants: The Role of Proton Pumps and $Na/H^+$-Antiporters, *Plant Physiol.*, 148:425-433, (1996).

Rea, P.A. and Turner, J.C., "Tonoplast Adenosine Triphosphatase and Inorganic Pyrophosphatase," *Method in Plant Biochemistry*, 3:385-405, (1990).

Rodriguez-Navarro, A. and Ramos, J., "Dual System for Potassium Transport in *Saccharomyces cerevisiae*," *Journal of Bacteriology*, 159(3):940-945, (1984).

Sandler, S.J., et al., "Inhibition of Gene Expression in Transformed Plants by Antisense RNA," *Plant Molecular Biology*, 11:301-310, (1988).

Schiefelbein, et al., Pollen Tube and Root-Hair Tip Growth is Disrupted in a Mutant of *Arabidopsis thaliana*, *Plant Physiol.*, 103:979-985, (1993).

Schneider, B.L., et al., "Use of Polymerase Chain Reaction Epitope Tagging for Protein Tagging in *Saccharomyces cerevisiae*," *Yeast*, 11(13):1265-1274, (1995).

Schumaker, K.S. and Sze, H., "A $Ca^{2+}/H^+$ Anitport System Driven by the Proton Electrochemical Gradient of a Tonoplast $H^+$-ATPase From Oat Roots," *Plant Physiol.*, 79: 1111-1117 (1985).

Sheveleva, E., et al., "Increased Salt and Drought Tolerance by D-Ononitol Production in Transgenic *Nicotiana tabacum* L.," *Plant Physiol.*, 115:1211-1219, (1997).

Sorin, A., et al., "PMR1, a $Ca^{2+}$-AtPase in Yeast Golgi, Has Properties Distinct From Sarco/Endoplasmic Reticulum and Plasma Membrane Calcium Pumps," *The Journal of Biological Chemistry*, 272(15):9895-9901, (1997).

Sugita, K., et al., "A Transformation Vector for the Production of Marker-Free Transgenic Plants Containing a Single Copy Transgene at High Frequency," *Plant Journal*, 22(5): 461-469 (2000).

Sze, et al. "Energization of Plant Cell Membranes by $H^+$-Pumping ATPases: Regulation and Biosynthesis,", *The Plant Cell*, 11:677-689, (1999).

van der Krol, A.R., et al., "Inhibition of Flower Pigmentation by Antisense CHS Genes: Promoter and Minimal Sequence Requirements for the Antisense Effect," 14:457-466, (1990).

Wu, S.J., et al., "SOS1, A Genetic Locus Essential for Salt Tolerance and Potassium Acquisition," *The Plant Cell*, 8:617-627, (1996).

Zemo, D.A. and McCabem, J.T., "Transcriptional Responses of the Rat Vasopressin Gene to Acute and Repeated Acute Osmotic Stress," *Neuroscience Research*, 44:45-50, (2002).

Zhen, R.G., et al., "Aminomethylenediphosphonate: A Potent Type=Specific Inhibitor of Both Plant and Phototrophic Bacterial $H^+$-Pyrophosphatases," *Plant Physiol.*, 104:153-159, (1994).

Zhen, R.G., et al., "Localization of Cytosolically Oriented Maleimide-Reactive Domain of Vacuolar $H^+$-Pyrophosphatase," *The Journal of Biological Chemistry*, 269(37):23342-23350, (1994).

Zhen, R.G., et al., "The Molecular and Biochemical Basis of Pyrophosphate-Energized Proton Translocation at the Vacuolar Membrane," *Advances in Botanical Research, The Plant Vacuole*, 25:298-337, (1997).

Hung, S., et al., "Vacuolar H+-Pyrophosphatase cDNA (Accession No. U31467) from Etiolated Mung Bean Seedlings," Plant Gene Register PGR 95-082, *Plant Physiol.*, 109:1125-1127 (1995).

Ikeda, M., et al., "A Vacuolar H+-Pyrophosphatase in *Acetabularia acetabulum*: Molecular Cloning and Comparison with Higher Plants and a Bacterium," *J. of Exp. Botany*, 50(330):139-140 (1999).

Nakanishi, Y. et al., "Molecular Cloning and Sequencing of the cDNA for Vacuolar H+-Pyrophosphatase from *Chara corallina*," *Biochimica et Biophysica Acta*, 1418:245-250 (1999).

Sakakibara, Y. et al., "Identification of the Gene Structure and Promoter Region of H+-Translocating Inorganic Pyrophosphatase in Rice (*Oryza saliva* L.)," *Biochimica et Biophysica Acta*, 1444:117-124 (1999).

Sakakibara, Y. et al., "Isolation and Characterization of cDNAs encoding Vacuolar H+-Pyrophosphatase Isoforms From Rice (*Oryza saliva* L.)," *Plant Molecular Biol.*, 31:1029-1038 (1996).

Smart, L.B., et al., "Genes Involved in Osmoregulation During Turgor-Driven Cell Expansion of Developing Cotton Fibers Are Differentially Regulated," *Plant Physiol.*, 116:1539-1549 (1998).

Suzuki, Y., et al., "Molecular Cloning of Vacuolar H+-Pyrophosphatase and Its Expression During the Development of Pear Fruit," *Plant Cell Physiol.*, 40(8):900-904 (1999).

Tanaka, Y., et al., "Molecular Cloning of cDNA for Vacuolar Membrane Proton-Translocating Inorganic Pyrophosphatase in *Hordeum vulgare*," *Biochem & Biophys. Res. Comm.*, 190(3):1110-1114 (1993).

Barkla, B.J. And Pantoja, O., "Physiology of Ion Transport across the Tonoplast of Higher Plants," *Annu. Rev. Plant Physiol. Plant Mol. Biol.*, 47:159-184 (1996).

Kay, R., et al., "Duplication of CaMV 35S promoter sequences creates a strong enhancer for plant genes," *Science*, 236:1299-1302 (1987).

Abdullah, R., et al., "Efficient Plant Regeneration From Rice Protoplasts Through Somatic Embryogenesis," *Bio/Technology*, 4:1087-1090 (1986).

Abel, S., et al., "Phosphate Sensing in Higher Plants," *Physiol. Plant.*, 115:1-8 (2002).

Altschul, S.F., et al., "Gapped BLAST and PSI-BLAST: A New Generation of Protein Database Search Programs," *Nucleic Acids Research*, 25(17):3389-3402, (1997).

Arango, M., et al., "The Plasma Membrane Proton Pump ATPase: The Significance of Gene Subfamilies," *Planta*, 216:355-365 (2003).

Bouche-Pillon, et al., "Immunolocalization of the Plasma Membrane H+-ATPase in Minor Veins of *Vicia faba* in Relation to Phloem Loading," *Plant Physiol.*, 105:691-697 (1994).

Brini, F., et al., "Cloning and Characterization of a Wheat Vacuolar Cation/Proton Antiporter and Pyrophosphatase Proton Pump," *Plant Physiology and Biochemistry*, 43(4): 347-354 (2005).

Cao, J., et al., "Regeneration of Herbicide Resistant Transgenic Rice Plant Following Microprojectilemediated Transformation of Suspension Culture Cells," *Plant Cell Rep.*, 11:586-591 (1992).

Clough, S.J. and Bent, A.F. "Floral Dip: A Simplified Method for Agrobacterium-Mediated Transformation of *Arabidopsis thaliana*," *Plant J.*, 16:735-743 (1998).

Drozdowicz, Y.M. and Rea, P.A., "Vacuolar H+-Pyrophosphatases: From Evolutionary Backwaters Into Mainstream," *Trends Plant Sci.*, 6(5):206-211 (2001).

Estelle, M. and Somerville, C., "Auxin-Resistant Mutants of *Arabidopsis thaliana* with an Altered Morphology," *Mol. Gen. Genet.*, 206:200-206 (1987).

Gahoonia, T.S. and Nielsen, N.E., "Root Traits As Tools for Creating Phosphorus Efficient Crop Varieties," *Plant Soil*, 260:47-57 (2004).

Gaxiola, R., et al., "Ectopic Overexpression in Tomato of the *Arabidopsis* AVP1 Gene Results in Drought Tolerance," *Plant Biology*, (Jul. 2003) [online], Retrieved from the Internet: URL: <http//abstracts.aspb.org/pb2003/public/P33/0948.html>.

Gaxiola, R., et al., "Increased Size, Salt and Drought Tolerance in *A. thaliana* Overexpressing AVP1 Vacuolar H+-Pyrophosphatase," *Plant Biology*, (Jul. 2001)[online], Retrieved from the Internet: URL: <http://abstracts.aspb.org/pub2001/public/P32/0206.html>.

Gaxiola, R.A., et al., "Plant Proton Pumps," *FEBS Lett.*, 581:2204-2214 (2007).

Gillooly, J.F., et al., "The Metabolic Basis of Whole-Organism RNA and Phosphorus Content," *Proc. Natl. Acad. Sci. USA*, 102(33):11923-11927 (2005).

Hammond, J.P., et al., "Genetic Responses to Phosphorus Deficiency," *Ann. Bot.*, 94:323-332 (2004).

Härtel, H., et al., "DGD1-Independent Biosynthesis of Extraplastidic Galactolipids After Phosphate Deprivation in *Arabidopsis?*," *Proc. Natl. Acad. Sci. USA*, 97(19):10649-10654 (2000).

Hermans, C., et al., "How Do Plants Respond to Nutrient Shortage by Biomass Allocation?," *Trends Plant Sci.*, 11(12):610-617 (2006).

Holford, I.C.R., "Soil Phosphorus: Its Measurements and Its Uptake by Plants," *Aust. J. Soil Res.*, 35:227-239 (1997).

Ikeda, M. et al., "A Vacuolar H+-pyrophosphatase in *Acetabularia acetabulum*: Molecular Cloning and Comparison with Higher Plants and a Bacterium," *Journal of Experimental Botany*, 50(330):139-140 (1999).

Kausch, A.P., et al., "Effects of Microprojectile Bombardment on Embryogenic Suspension Cell Cultures of Maize (*Zea mays* L.) Used for Genetic Transformation," *Planta*, 196:501-509 (1995).

Kochian, L., et al.. "How Do Crop Plants Tolerate Acid Soils? Mechanisms of Aluminium Tolerance and Phosphorus Efficiency," *Annu. Rev. Plant Biol.*, 55:459-493 (2004).

López-Bucio, et al., "Phosphate Availability Alters Architecture and Causes Changes in Hormone Sensitivity in the *Arabidopsis* Root System," *Plant Physiol.*, 129:244-256 (2002).

Maruyama, C. et al., "Structural Studies of the Vacuolar H+-Pyrophosphatase: Sequence Analysis and Identification of the Residues Modified by Fluorescent Cyclohexylcarbodiimide and Maleimide," *Plant Cell Physiol.* 39(10):1045-1053 (1998).

McSteen, P. and Leyser, O., "Shoot Branching," *Annu. Rev. Plant Biol.*, 56:353-374 (2005).

Meyerowitz, E.M., "In Situ Hybridization to RNA in Plant Tissue," *Plant Molec. Biol. Rep.*, 5(1):242-250, (1987).

Misson, J., et al., "A Genome-Wide Transcriptional Analysis Using *Arabidopsis thaliana* Affymetrix Gene Chips Determined Plant Responses to Phosphate Deprivation," *Proc. Natl. Acad. Sci. USA*, 102(33):11934-11939 (2005).

Muchhal, U.S., et al., "Phosphate Transporters From the Higher Plant *Arabidopsis thaliana*," *Proc. Natl. Acad. Sci. USA*, 93:10519-10523 (1996).

Murashige, T. and Skoog, F., "A Revised Medium for Rapid Growth and Bioassays With Tobacco Tissue Culture," *Physiol. Plant.*, 15:473-497 (1962).

Murphy, A., et al., "Early Copper-Induced Leakage of K+ From *Arabidopsis* Seedlings Is Mediated by Ion Channels and Coupled to Citrate Efflux," *Plant Physiol.*, 121:1375-1382 (1999).

Murphy, J. and Riley, J.P., "A Modified Single Solution Method for the Determination of Phosphate in Natural Waters," *Anal. Chim. Acta*, 27:31-36 (1962).

Nakanishi, Y. and Maeshima, M., "Molecular Cloning of Vacuolar H+-Pyrophosphatase and Its Developmental Expression in Growing Hypocotyl of Mung Bean," *Plant Physiol.* 116:589-597 (1998).

Raghothama, K.G., "Phosphate Acquisition," *Annu. Rev. Plant Physiol. Plant Mol. Biol.*, 50:665-693 (1999).

Rea, P.A., et al., "Vacuolar H(+)-Translocating Pyrophosphatases: A New Category of Ion Translocase," *Trends Biochem. Sci.*, 17:348-353 (1992).

Rodríguez-Navarro, A. and Ramos, J., "Dual System for Potassium Transport in *Saccharomyces cerevisiae*," *Journal of Bacteriology*, 159(3):940-945, (1984).

Sánchez-Calderón, L., et al., "Characterization of Low Phosphorus Insensitive Mutants Reveals a Crosstalk Between Low Phosphorus-Induced Determinate Root Development and Activation of Genes Involved in the Adaptation of *Arabidopsis* to Phosphorus Deficiency," *Plant Physiol.*, 140:879-889 (2006).

Sarafian, V., et al., "Radiation-Inactivation Analysis of Vacuolar Proton Atpase and Proton Pyrophosphatase From *Beta vulgaris* L. Functional sizes for Substrate Hydrolysis and for Proton Transport," *Biochemical Journal*, 283(2): 493-497 (1992).

Vance, C.P., et al., "Phosphorus Acquisition and Use: Critical Adaptations by Plants for Securing a Nonrenewable Resource," *New Phytologist*, 157:423-447 (2003).

Ward, J.M., et al., "Dissociation and Reassembly of the Vacuolar H+-ATPase Complex From Oat Roots," *Plant Physiol.*, 99:161-169 (1992).

Xiang, C., et al., "A Mini Binary Vector Series for Plant Transformation," *Plant Mol. Biol.*, 40:711-717 (1999).

Yan, F., et al., "Adaptation of H+-Pumping and Plasma Membrane H+ ATPase Activity in Proteoid Roots of White Lupin Under Phosphate Deficiency," *Plant Physiol.*, 129:50-63 (2002).

Yelenosky, G. and Guy, C.L., "Freezing Tolerance of Citrus, Spinach, and Petunia Leaf Tissue," *Plant Physiol.* 89:444-451 (1989).

Zhang, J., et al., "Improving Drought Tolerance in *Medicago truncatula* Via Translational Genomics," *Plant Biology*, (Jul. 2007)[online] Retrieved from the Internet: URL: <http://abstracts.aspb.org/pb2007/public/P09/P09019.html>.

Zhu, Y., et al., "A Link Between Citrate and Proton Release by Protcoid Roots of White Lupin (*Lupinus albus* L.) Grown Under Phosphorus-Deficient Conditions," *Plant Cell Physiol.*, 46(6):892-901 (2005).

Office Action, U.S. Appl. No. 11/135,165, Dated: Oct. 31, 2006.
Office Action, U.S. Appl. No. 11/135,165, Dated: Jul. 25, 2007.
Office Action, U.S. Appl. No. 11/135,165 Dated: Jun. 6, 2008.
Office Action, U.S. Appl. No. 11/135,165, Dated: Oct. 22, 2009.
Office Action Made Final, U.S. Appl. No. 11/135,165 Dated: Aug. 2, 2010.
Office Action, U.S. Appl. No. 11/135,165, Dated: Feb. 28, 2011.
Notice of Abandonment, U.S. Appl. No. 09/934,088, Dated: Jul. 27, 2005.
Office Action, U.S. Appl. No. 09/934,088 Dated: Dec. 22, 2004.
Office Action, U.S. Appl. No. 09/934,088, Dated: Sep. 24, 2003.
Notice of Allowance, U.S. Appl. No. 10/344,658, Dated: Jan. 16, 2009.
Office Action—Advisoty Action, U.S. Appl. No. 10/344,658, Dated: Dec. 9, 2008.
Office Action—Interview Summary, U.S. Appl. No, 10/344,658, Dated: Oct. 27, 2008.
Office Action, U.S. Appl. No. 10/344,658, Dated: Sep. 18, 2008.
Examiner-Initiated Interview Summary—Office Action, U.S. Appl. No. 10/344,658, Dated: Mar. 18, 2008.
Office Action Made Final, U.S. Appl. No. 10/344,658, Dated: Mar. 10, 2008.
Office Action U.S. Appl. No. 10/344,658, Dated: Aug. 6, 2007.
Office Action, U.S. Appl. No. 10/344,658, Dated: Nov. 14, 2006.
Interview Summary—Office Action, U.S. Appl. No. 10/344,658, Dated: Aug. 1, 2006.
Office Action Made Final, U.S. Appl. No. 10 /344,658, Dated: May 17, 2006.
Office Action, U.S. Appl. No. 10/344,658, Dated: Nov. 3, 2005.
Office Action—Notice of Panel Decision from Pre-Appeal Brief Review, U.S. Appl. No. 11/890,795, Dated: Mar. 28, 2011.
Office Action Made Final, U.S. Appl. No. 11/890,795, Dated: May 26, 2010.
Office Action, U.S. Appl. No. 11/890,795, Dated: Oct. 13, 2009.
Office Action Made Final, U.S. Appl. No. 11/890,795, Dated: Apr. 29, 2009.
Office Action, U.S. Appl. No. 11/890,795, Dated: Sep. 15, 2008.
International Search Report, PCT/US01/41806, mailed Dec. 19, 2001.
International Preliminary Examination Report, PCT/US01/41806, completed Jun. 17, 2003.
International Search Report, PCT/US01/09548 mailed Jul. 31, 2001.
International Preliminary Examination Report (IPER), PCT/US01/09548, completed Aug. 1, 2003.
Office Action, U.S. Appl. No. 12/384,115, mailed Feb. 24, 2010.
Notice of Allowance, U.S. Appl. No. 12/384,115, dated May 27, 2011.
Office Action, U.S. Appl. No. 12/384,115, mailed Sep. 16, 2010.
Office Action, CA 2,419,901, dated Nov. 18, 2010.
Office Action, CA 2,419,901, dated Mar. 16, 2009.
Office Action, CA 2,390,719, dated Nov. 12, 2010.
Office Action, CA 2,390,719, dated Mar. 10, 2009.
Office Action, CA 2,418,127, dated Nov. 12, 2010.
Office Action, CA 2,418,127, dated Mar. 10, 2009.
International Search Report with Written Opinion, PCT/US2008/009091, Mail date: Oct. 30, 2008.
International Preliminary Report on Patentability, International Application No. PCT/US2008/009091, Dated: Feb. 9, 2010.

* cited by examiner

```
AtNhx1    1                                                                                    0
HsNhe-6   1    M A R R G W R R A P L R R G V G S S P R A R R L M R P L W L L L A              33
ScNhx1    1    M L S K V L L N I A F K V L L T T - - - A K R A V D P D D D D E L              30

AtNhx1    1                                        M L D S L V S K L P S L S T S              15
HsNhe-6   34   V G V F D W A G A S D G G G G E A R A M D E E I V S E K Q A E E S              66
ScNhx1    31   L P S P D L P G S D D P I A G - - - - D P D V D L N P V T E E M                58

AtNhx1    16   D H A S V V A L N L F V A L L C A C I V L G H L L E E N - - R W M              46
HsNhe-6   67   H R Q D S A N L L I F I L L L T L T I I W L F K H R R A R F L                  99
ScNhx1    59   F S - - S W A L F I M L L L L I S A L W S S Y Y L T Q K R I R A V              89

AtNhx1    47   N E S I T A L L I G L G T G V T I L L I S K G K S S H L - - - - -              74
HsNhe-6   100  H E T G L A M I Y G L L V G L V L H Y G - I H V P S D V N N V T L              131
ScNhx1    90   H E T V L S I F Y G M V I G L I I R M S P G H Y I Q D T - - - - -              117

AtNhx1    75   - - - - - - - - - L V F S E D L F I Y L L P P I I F N A G                      95
HsNhe-6   132  S C E V Q S S P T T L L V T F D P E V F F N I L L P P I I F Y A G              164
ScNhx1    118  - - - - - - - - - - V T F N S S Y F F N V L L P P I I L N S G                  138

AtNhx1    96   F Q V K K K Q F F R N F V T I M L G A V G T I S C T I I S L G                  128
HsNhe-6   165  Y S L K R R H F F R N L G S I L A Y A F L G T A I S C F V I G S I                197
ScNhx1    139  Y E L N Q V N F N N M L S I L I F A I P G T F I S A V V I G I I                 171

AtNhx1    129  V T - - - - - Q F F K K L D I G T F D L G D Y L A I G A I F A A T              156
HsNhe-6   198  M Y G G V T L M K V T G Q L A G D F Y F T D C L L F G A I V S A T              230
ScNhx1    172  L Y - - - - - I W T F L G L E S I D I S F A D A M S V G A T L S A T              200

AtNhx1    157  D S V C T L Q V L N Q D E T - P L Y S L V F G E G V V N D A T S              188
HsNhe-6        D P V T V L A F H E L Q V D V E L Y A L L F G E S V L N D A V A                263
ScNhx1    201  D P V T I L S I F N A Y K V D P K L Y T I I F G E S L L N D A I S              233

AtNhx1    189  V V V F N A I Q S F D L T H - - L - - - N H E A A F H L L G N F L              216
HsNhe-6   264  I V L S S S I V A Y Q P A G D N S H T F D V T A M F K S I G I F L              296
ScNhx1    234  I V M F E T C Q K F H G Q P - A T - - F S S - - V F E G A G L F L              261

AtNhx1    217  Y L F L L S T L L G A A T G L I S A Y V I K K L Y F G R H S T D R              249
HsNhe-6   297  G I F S G S F A M G A A T G V V T A L V T K F T K L - R E F Q L L              328
ScNhx1    262  M T F S V S L L I G V L I G I L V A L L K H T H I - R R Y P Q I

AtNhx1    250  E V A L M M L M A Y L S Y M L A E L F D L S G I L T V F F C G I V              282
HsNhe-6   329  E T G L F F L M S W S T F L L A E A W G F T G V V A V L F C G I T              361
ScNhx1    294  E S C L I L L I A Y E S Y F F S N G C H M S G I V S L L F C G I T              326

AtNhx1    283  M S H Y T W H N V T E S S R I T T K H T F A T L S F L A E T F F F              315
HsNhe-6   362  Q A H Y T Y N N L S T E S Q H R T K Q L F E L L N F L A E N F I F              394
ScNhx1    327  L K H Y A Y Y N M S R R S Q I T I K Y I F Q L L A R S E N F I F              359

AtNhx1    316  L Y V G M D A L D I D K W R S V S D T P G T S I A V S S I L M G L              348
HsNhe-6   395  S Y M G L T L F T F Q N H - - V F N P T F V V G A F V A I F L - -              423
ScNhx1    360  I Y L G L E L F T E V E L - - V Y K P L L I I V A A I S I C V - -              388

AtNhx1    349  V M V G R A A F V F P L S F L S N L A K K N Q - - - - - S - - - -              372
HsNhe-6   424  - - - G R A A N I Y P L S L L L N L G R R S K - - - - - - - - - -              443
ScNhx1    389  -  - A R W C A V F P L S - Q F V N W I Y R V K T I R S M S G I T              417

AtNhx1    373  - - - - - - E K I N F N M Q V V I W W S G L M R G A V S M A L A Y              399
HsNhe-6   444  - - - - - - - - - I G S N F Q H M M M F A G - L R G A M A F A L A I              467
ScNhx1    418  G E N I S V P D E I P Y N Y Q M M T F W A G - L R G A V G V A L A              449

AtNhx1    400  N K F T R A G H T D V R G N A I M I T S T I T V C L F S T V V F G              432
HsNhe-6   468  R D T A T Y A R - Q M M F S T T L I V F F T W V F G G T T A                    499
ScNhx1    450  L G I Q G E Y K - - F T L L A T V L V V V L T V I I F G G T T A                480

AtNhx1    433  M L T K P L I S Y L L P H Q N A T T - - - - S M L S D D N T P K S              461
HsNhe-6   500  M L S C L H I R V G V D S D Q E H L G V P E N E R R T T K A E S A              532
ScNhx1    481  G M L E V L N I K T G C I S E E D T S - - - - D D E F D I E A P R              509

AtNhx1    462  I H I P L L D - - Q D S F I E P S G N H N V P - - - - R P D S I R              488
HsNhe-6   533  W L F R M W Y N F D H N Y L K P L L T H S G P P L T T T L P A C C              565
ScNhx1    510  A I N L L N G S - S I Q T D L G P Y S D N N S P D I S I D Q F A V              541

AtNhx1    489  G F L T R P T R T V H Y Y W R Q F D D S F M R P - V F G G R G F V              520
HsNhe-6   566  G P I A R C L T S P Q A Y E N Q E Q L K D D D S D L I L N D G D I              598
ScNhx1    542  S S N K N L P N N I S T T G G N T F G G L N E T E N T S P N P A R              574

AtNhx1    521  P F V P G S P T E R N P P D L S K A                                            538
HsNhe-6   599  S L T Y G D S T V N T E P A T S A P R R F M G N S S E D A L D R                631
ScNhx1    575  S S M D K R N L R D K L G T I F N S D S Q W F Q N - - F D E Q V L              605

HsNhe-6   632  E L A F G D H E L V I R G T R L V L P M D D S E P P L N L L D N T              664
ScNhx1    606  K P V F L D N V S P S L Q D S A T Q S P A D F S S Q N H                        633

HsNhe-6   665  R H G P A                                                                     669
```

FIGURE 2

```
 -155   CTTAGATTTATCTTTGAGTCCCGAAACATCGAGGAACGCCTTCGAATCCCTCTCTCTCTGTGTGTTCTCTGTGTTCTCTCTCTCCCG   -67
  -66   CGAAGCGGTTCTCTTTCTTTTGTTTATTTGTTTTTATTTGTTTTTCTCTTATACGGAGGAGAGAAGATGGTGGCGCCTGCTTTGTTACCGGAG    27
                                                                   1-MetValAlaProAlaLeuLeuProGlu   9
   28   CTCTGGACGGAGATCCTTGTACCGATTTGTGCGGTGATTGGTATCGCCTTTTCGCTTTTCCAATGGTACGTTGTATCTCGCGTGAAACTCACC   120
   10   LeuTrpThrGluIleLeuValProIleCysAlaValIleGlyIleAlaPheSerLeuPheGlnTrpTyrValValSerArgValLysLeuThr    40
  121   TCTGACCTCCGGCGCATCGTCTTCCGGTGGAGCTAACAATGGGAAGAATGGATACGGTGATTATCTAATCGAGGAAGAGGAAGGTGTTAATGAC   213
   41   SerAspLeuGlyAlaSerSerSerGlyGlyAlaAsnAsnGlyLysAsnGlyTyrGlyAspTyrLeuIleGluGluGluGluGlyValAsnAsp    71
  213   CAGACTCTTCTCGCTAACTGCGCTGAGATTCAGACTGCTATTTCCAACGTGCAACTTCATTCCTATTCACGGAGTACAAATATGTTGGTGTC    306
   72   GlnSerValValAlaLysCysAlaGluIleGlnThrAlaIleSerGluGlyAlaThrSerPheLeuPheThrGluTyrLysTyrValGlyVal   102
  307   TTCATGATTTTCTTTGCTGCTGTTATCTTTGTTTTTCCTCGGCTCTGTTGAGGGATTCAGCACTGATAACAAGCCTTGTACTTACGACACCACC   399
  103   PheMetIlePhePheAlaAlaValIlePheValPheLeuGlySerValGluGlyPheSerThrAspAsnLysProCysThrTyrAspThrThr   133
  400   AGAACCTGCAAGCCTGCATTGGCTACTGCAGCTTTCAGTACCATTGCTTTCGTGCTTGGTGCTGTTACCTCTGTTCTATCTGGTTTCCTTGGG   492
  134   ArgThrCysLysProAlaLeuAlaThrAlaAlaPheSerThrIleAlaPheValLeuGlyAlaValThrSerValLeuSerGlyPheLeuGly   164
  493   ATGAAGATTGCTACATACGCTAATGCTAGGACCACTTTCGAGGCGGAGGAAACGTCTTGGAAAGGCGTTCATTGTTGCATTCAGGTCTGCTGCT   585
  165   MetLysIleAlaThrTyrAlaAsnAlaArgThrThrLeuGluAlaArgLysGlyValGlyLysAlaPheIleValAlaPheArgSerGlyAla   195
  586   GTGATGGGTTTCCTTCTTGCAGCGAGTGGTCTATTGGTGCTTTACATTACTATCAATGTGTTCAAGATCTATTACGGAGATGACTGGGAAGGT   678
  196   ValMetGlyPheLeuLeuAlaAlaSerGlyLeuLeuValLeuTyrIleThrIleAsnValPheLysIleTyrTyrGlyAspAspTrpGluGly   226
  679   CTTTTTGAGGCTATTACTGGTTATGGTCTTGGTGGGTCTTCCATGGCTCTCTTTGGCCGTGTTGGTGGTGGGATCTACACTAAGGCTGCTGAT   771
  227   LeuPheGluAlaIleThrGlyTyrGlyLeuGlyGlySerSerMetAlaLeuPheGlyArgValGlyGlyGlyIleTyrThrLysAlaAlaAsp   257
  772   GTCGGCGCTGACCTTGTCGGTAAAATTGAGAGGAATATTCCAGAGGATGATCCAAGAAACCCAGCTGTCATTGCTGATAATGTCGGTGACAAT   864
  258   ValGlyAlaAspLeuValGlyLysIleGluArgAsnIleProGluAspAspProArgAsnProAlaValIleAlaAspAsnValGlyAspAsn   288
  865   GTTGGTGACATTGCTGGTATGGGATCTGATCTCTTTGGATCATATGCTGAAGCATCATGCGCTGCTCTTGTTGTTGCCTCGATCTCATCTTTC   957
  289   ValGlyAspIleAlaGlyMetGlySerAspLeuPheGlySerTyrAlaGluAlaSerCysAlaAlaLeuValValAlaSerIleSerSerPhe   319
  958   GGAATCAACCACGACTTCACTGCCATGTGCTACCCATTGCTCATCAGTTCAATGGGAATCTTGGTTTGTTTGATCACAACTCTCTTTGCCACT   1050
  320   GlyIleAsnHisAspPheThrAlaMetCysTyrProLeuLeuIleSerSerMetGlyIleLeuValCysLeuIleThrThrLeuPheAlaThr   350
 1051   GACTTCTTTGAGATTAAGCTTGTCAAGGAGATTGAACCAGCATTGAAGAACCAGCTCATTATCTCAACTGTTATTATGACTGTTGGTATTGCT   1143
  351   AspPhePheGluIleLysLeuValLysGluIleGluProAlaLeuLysAsnGlnLeuIleIleSerThrValIleMetThrValGlyIleAla   381
 1144   ATTGTGTCATGGGTTGGCTTACCGACCTCCTTTACCATCTTCAACTTTGGAACACAAAAAGTTGTCAAGAACTGGCAGCTATTCCTTTGTGTT   1236
  382   IleValSerTrpValGlyLeuProThrSerPheThrIlePheAsnPheGlyThrGlnLysValValLysAsnTrpGlnLeuPheLeuCysVal   412
 1237   TGTGTTGGTCTTTGGGCTGGACTCATTATTGGTTTCGTCACTGAGTACTACACTAGTAACGCCTACAGCCCTGTGCAAGATGTTGCAGATTCA   1329
  413   CysValGlyLeuTrpAlaGlyLeuIleIleGlyPheValThrGluTyrTyrThrSerAsnAlaTyrSerProValGlnAspValAlaAspSer   443
 1330   TGCAGAACTGGTGCAGCTACCAATGTTATCTTCGGCCTTGCTCTTGGTTACAAATCCGTCATTATTCCAATCTTTGCTATTGCTATAGTATA   1422
  444   CysArgThrGlyAlaAlaThrAsnValIlePheGlyLeuAlaLeuGlyTyrLysSerValIleIleProIlePheAlaIleAlaIleSerIle   474
 1423   TTCGTTAGCTTCAGCTTTGCTGCTATGTATGGTGTTGCTGTTGCTGCTCTTGGTATGCTCAGTACCATTGCCACTGGTTTGGCAATTGATGCT   1515
  475   PheValSerPheSerPheAlaAlaMetTyrGlyValAlaValAlaAlaLeuGlyMetLeuSerThrIleAlaThrGlyLeuAlaIleAspAla   505
 1516   TATGGTCCCATCAGTGACAATGCTGGTGGTATTGCTGAAATGGCTGGAATGAGCCACCGCATCCGTGAAAGAACTGATGCTCTTGATGCCGCT   1608
  506   TyrGlyProIleSerAspAsnAlaGlyGlyIleAlaGluMetAlaGlyMetSerHisArgIleArgGluArgThrAspAlaLeuAspAlaAla   536
 1609   GGAAACACCACTGCTGCTATTGGAAAGGGATTTGCCATTGGCTCTGCTGCCCTAGTCTCCTTGGCTCTCTTTGGTGCCTTTGTGAGCCGTGCA   1701
  537   GlyAsnThrThrAlaAlaIleGlyLysGlyPheAlaIleGlySerAlaAlaLeuValSerLeuAlaLeuPheGlyAlaPheValSerArgAla   567
 1702   GGGATCCACACCGTAGATGTTTTGACCCCTAAAGTTATCATTGGGCTCCTTGTTGGTGCCATGCTTCCTTACTGGTTCTCTGCCATGACAATG   1794
  568   GlyIleHisThrValAspValLeuThrProLysValIleIleGlyLeuLeuValGlyAlaMetLeuProTyrTrpPheSerAlaMetThrMet   598
 1795   AAGAGTGTGGGAAGTGCAGCTCTTAAGATGGTTGAAGAAGTTCGCAGGCAGTTCAACACCATCCCTGGACTTATGGAAGGAACCGCAAAACCA   1887
  599   LysSerValGlySerAlaAlaLeuLysMetValGluGluValArgArgGlnPheAsnThrIleProGlyLeuMetGluGlyThrAlaLysPro   629
 1888   GACTACGCCACATGTGTCAAGATCTCCACCGATGCTTCCATCAAGGAAATGATACCTCCTGGTTGCCTTGTCATGCTCACACCTCTCATTGTT   1980
  630   AspTyrAlaThrCysValLysIleSerThrAspAlaSerIleLysGluMetIleProProGlyCysLeuValMetLeuThrProLeuIleVal   660
 1981   GGTTTCTTCTTTGGAGTTGAGACCCTCTCTGGTGTCCTCGCCGGATCTCTTGTATCCGGTGTTCAGATCGCCATATCAGCATCTAACACTGGT   2073
  661   GlyPhePhePheGlyValGluThrLeuSerGlyValLeuAlaGlySerLeuValSerGlyValGlnIleAlaIleSerAlaSerAsnThrGly   691
 2074   GGTGCCGGGACAACGCCAAGAAATACATCGAGGCGGTGTATCAGAGCACGCAAAGAGCCTTGGACCAAAGGGTTCAGAGCCACACAAGGCA   2166
  692   GlyAlaTrpAspAsnAlaLysLysTyrIleGluAlaGlyValSerGluHisAlaLysSerLeuGlyProLysGlySerGluProHisLysAla   722
 2167   GCTGTCATTGGAGACACAATTGGAGACCCATTGAAGGATACTTCAGGATCTCCATTGAACATCCTCATCAAGCTCATGGCTGTTGAGTCTCTT   2259
  723   AlaValIleGlyAspThrIleGlyAspProLeuLysAspThrSerGlyProSerLeuAsnIleLeuIleLysLeuMetAlaValGluSerLeu   753
 2260   GTCTTTGCTCCCTTCTTCGCCACTCACGGTGGTATCCTTTTCAAGTACTTCTAAACTCAATCCGAGGGAAGAAGATGACGATGATGAAGAAGA   2352
  754   ValPheAlaProPhePheAlaThrHisGlyGlyIleLeuPheLysTyrPhe-770
 2353   AGAAGATGATGATGGCGATCGATTCTAAACTTTCTTTTTTACCATTCTTATTTTCGTTTACCGTAGGTGGTTAAAAAACCTTTTTGTTGATGA   2445
 2446   GGCTCATTTAAAGAACCAACCAAATGATGTTTCTTTCTCTCACTCTCTGTCTTTCTGTTTTCTTTTTGTTCTGTTTAGAATTTAGAAATCCAC   2538
 2539   CAAGTATTCGGTCGAGACTTGTTTTAGCCGTTACTTTCTGCTGCTTATATTTCCTAAATTGGTTGTCTTCTTCGAAACATAATTGGAATTTAT   2631
 2632   TGTTACTGTTAGTCTAAAAAAAAAAAAA   2658
```

Figure 4

PLANT CELLS AND PLANTS OVEREXPRESSING VACUOLAR PROTON PYROPHOSPHATASES

RELATED APPLICATION(S)

This application is a continuation of U.S. application Ser. No. 09/834,998, filed Apr. 13, 2001, now abandoned which is a continuation of U.S. application Ser. No. 09/644,039, filed Aug. 22, 2000, now abandoned which claims the benefit under Title 35, U.S.C. §119(e), of U.S. Application No. 60/164,808 filed Nov. 10, 1999. The entire teachings of the above applications are incorporated herein by reference.

GOVERNMENT SUPPORT

The invention was supported, in whole or in part, by grants GM52414, DK54214, DK43495, DK51509, DK34854 and GM35010 from the National Institutes of Health and by grant MCB9317175 from the National Science Foundation. The Government has certain rights in the invention.

BACKGROUND OF THE INVENTION

The prospects for feeding humanity as we enter the new millennium are formidable. The progressive salinization of irrigated land compromises the future of agriculture in the most productive areas of our planet (Serrano, R., et al., *Crit. Rev. Plant Sci.*, 13:121-138 (1994)). Arid regions offer optimal photoperiod and temperature conditions for the growth of most crops, but suboptimal rainfall. Artificial irrigation has solved the problem in the short term. However, water supplies always contain some dissolved salt, which upon evaporation gradually accumulates on the soils.

To grow in saline environments, plants must maintain a much lower ratio of $Na^+/K^+$ in their cytoplasm than that present in the soil. A need exists for crops having increased tolerance to salt.

SUMMARY OF THE INVENTION

The present invention relates to a transgenic plant which is tolerant to a salt, comprising one or more plant cells transformed with exogenous nucleic acid which alters expression of vacuolar pyrophosphatase in the plant. In one embodiment, the exogenous nucleic acid encodes AVP1 or a homologue thereof. In another embodiment, the present invention relates to a transgenic plant which grows in a concentration of a salt that inhibits growth of a corresponding non-transgenic plant. In a particular embodiment, the transgenic plant is tolerant to sodium chloride (NaCl) and the NaCl concentration is from about 0.2M to about 0.3M. In a another embodiment, the present invention relates to a transgenic plant which is tolerant to salt comprising (containing within some or all of its cells) an exogenous nucleic acid construct which is designed to overexpress AVP1 or designed to down regulate endogenous pyrophosphatase. In yet another embodiment, the invention relates to a transgenic plant obtained by introducing into a plant exogenous nucleic acid which alters expression of vacuolar pyrophosphatase in the plant.

Also encompassed by the present invention are transgenic progeny and seeds of the transgenic plants described herein. Progeny transgenic plants grown from seed of transgenic plants are also described.

The present invention also relates to a construct comprising an AVP1 gene operably linked to a chimeric promoter designed to overexpress AVP1 or designed to down regulate endogenous pyrophosphatase. In one embodiment, the AVP1 gene is operably linked to a double tandem enhancer of a 35S promoter.

Plant cells (e.g., root cells, stem cell, leaf cells) comprising exogenous nucleic acid which alters expression of vacuolar pyrophosphatase in the plant cell are also the subject of the present invention.

Also encompassed by the present invention is a method of making a transgenic plant which is tolerant to salt comprising introducing into one or more cells of a plant exogenous nucleic acid which alters expression of vacuolar pyrophosphatase in the plant to yield transformed cells in the plant, thereby producing a transgenic plant which is tolerant to salt. For example, this can be carried out in a whole plant, seeds, leaves, roots or any other plant part. In one embodiment, the present invention relates to a method of making a transgenic plant which is tolerant to salt comprising introducing into one or more cells of a plant a nucleic acid construct which is designed to overexpress AVP1 to yield transformed cells thereby producing a transgenic plant which is tolerant to salt. The method can further comprise regenerating plants from the transformed cells to yield transgenic plants and selecting a transgenic plant which is tolerant to salt, thereby producing a transgenic plant which is tolerant to salt.

The present invention also relates to a method of making a transgenic plant which is larger than its corresponding wild type plant comprising introducing into one or more cells of a plant nucleic acid which alters expression of vacuolar pyrophosphatase in the plant to yield transformed cells, thereby producing a transgenic plant which is larger than its corresponding wild type. The method can further comprise regenerating plants from the transformed cells to yield transgenic plants and selecting a transgenic plant which is tolerant to salt, thereby producing a transgenic plant which is larger than its corresponding wild type.

Transgenic plants produced by the methods of making a transgenic plant as described herein are also a subject of the present invention.

The present invention relates to a method of bioremediating soil comprising growing one or more transgenic plants and/or progeny thereof in the soil, wherein the transgenic plants and/or progeny thereof comprise exogenous nucleic acid which alters expression of vacuolar pyrophosphatase in the plant. The transgenic plants grow in the soil, and in the process, take up cations from the soil. In one embodiment, the present invention relates to a method of removing one or more cations from a medium which can support plant growth (e.g., soil, water) comprising growing one or more transgenic plants and/or progeny thereof in the medium, wherein the transgenic plants and/or progeny thereof comprise exogenous nucleic acid which alters expression of vacuolar pyrophosphatase in the plant.

The present invention provides for a method of increasing the yield of a plant comprising introducing into one or more cells of a plant nucleic acid which alters expression of vacuolar pyrophosphatase in the plant to yield transformed cells, thereby increasing the yield of the plant. The method can further comprise regenerating plants from the transformed cells to yield transgenic plants and selecting a transgenic plant which is larger than its corresponding wild type plant, thereby producing a transgenic plant which is larger than its corresponding wild type plant.

Also encompassed by the present invention is a method of making a transgenic plant (e.g., an ornamental plant) having increased flower size compared to its corresponding wild type plant comprising introducing into one or more cells of a plant nucleic acid which alters expression of vacuolar pyrophosphatase in the plant to yield transformed cells, thereby producing a transgenic plant having increased flower size compared to its corresponding wild type plant.

The present invention also provides for a method of producing a transgenic plant which grows in salt water, such as water in which the salt concentration is equivalent to that of seawater (e.g., about 0.2M to about 0.4M), comprising introducing into one or more cells of a plant nucleic acid which alters expression of vacuolar pyrophosphatase in the plant to yield transformed cells, thereby producing a transgenic plant which grows in salt water. The method can further comprise regenerating plants from the transformed cells to yield transgenic plants and selecting a transgenic plant which is larger than its corresponding wild type plant, thereby producing a transgenic plant which can grow in salt water.

The transgenic plants of the present invention can also be used to produce double transgenic plants which are tolerant to salt (about 0.2M to about 0.4M salt concentration). In one embodiment, the present invention relates to a double transgenic plant which is tolerant to salt comprising one or more plant cells transformed with exogenous nucleic acid which alters expression of a vacuolar pyrophosphatase and an $Na^+/H^+$ antiporter in the plant. In one embodiment, the vacuolar pyrophosphatase is AVP1 or a homologue thereof and the $Na^+/H^+$ antiporter is AtNHX1 or a homologue thereof. The present invention further relates to a transgenic progeny of the double transgenic plant, as well as seeds produced by the transgenic plant and a progeny transgenic plant grown from the seed.

BRIEF DESCRIPTION OF THE DRAWINGS

FIG. 2 is alignment of the deduced amino acid sequences of NhX1 homologue from *Arabidopsis* AtNHX1 (SEQ ID NO: 1), human HsNHE-6 (SEQ ID NO: 2) and yeast ScNHX1 (SEQ ID NO:3); identical residues are in black boxes, and dashes indicate gaps in the sequence, * above alignment denote putative amiloride binding site from human NHE1 ($^{163}$DVF-FLFLLPPI$^{173}$) (SEQ ID NO: 4).

FIG. 4 depicts a nucleotide sequence of *Arabidopsis* cDNA (SEQ ID NO:6) encoding *Arabidopsis* vacuolar pyrophosphatase (AVP1) and the predicted amino acid sequence of AVP1 (SEQ ID NO:7) encoded by the nucleotide sequence.

DETAILED DESCRIPTION OF THE INVENTION

Figure 1A:
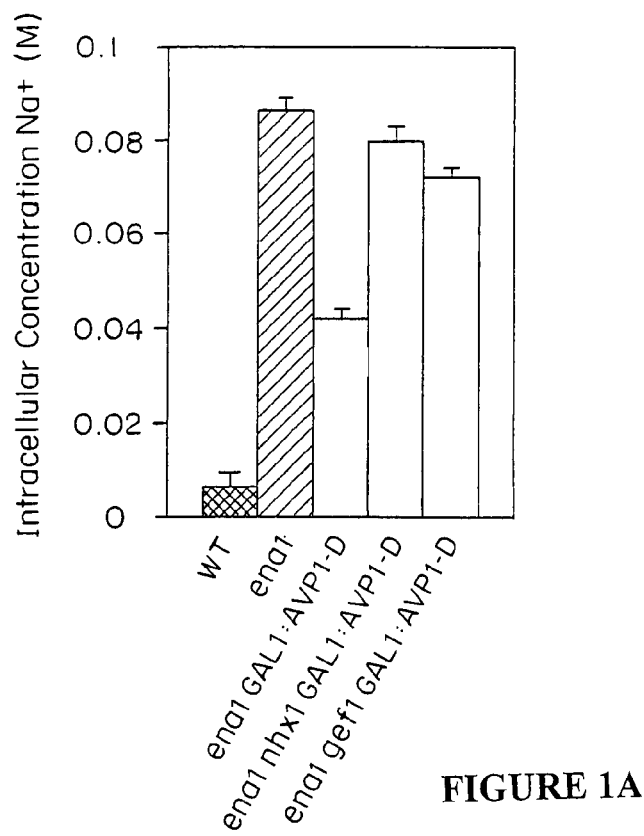
FIGS. 1A and 1B are bar graphs showing the intracellular $Na^+$ and $K^+$ contents of wild-type yeast strains and of yeast strains carrying various mutations affecting sodium tolerance; values are the mean of two determinations, and bars represent the standard deviations.

Producing salt-tolerant plants using genetic engineering requires the identification of the relevant genes. Physiological studies suggest that salt exclusion in the root and/or salt sequestration in the leaf cell vacuoles are critical determinants for salt tolerance (Kirsch, M., et al., *Plant Mol. Biol.*, 32:543-547 (1996)). Toxic concentrations of sodium chloride (NaCl) build up first in the fully expanded leaves where NaCl is compartmentalized in the vacuoles. Only after their loading capacity is surpassed, do the cytosolic and apoplasmic concentrations reach toxic levels, ultimately leading to loss of turgor, ergo plant death. It has been suggested that hyperacidification of the vacuolar lumen via the V-ATPase provides the extra protons required for a $Na^+/H^+$ exchange-activity leading to the detoxification of the cytosol (Tsiantis, M. S., et al., *Plant J.*, 9:729-736 (1996)). Salt stress increases both ATP- and pyrophosphate (PPi)-dependent $H^+$ transport in tonoplast vesicles from sunflower seedling roots. Salt treatments also induce an amiloride-sensitive $Na^+/H^+$ exchange activity (Ballesteros, E., et al., *Physiologia Plantarum*, 99:328-334 (1997)). In the halophyte *Mesembryanthemum crystallinum*, high NaCl stimulates the activities of both the vacuolar $H^+$-ATPase (V-ATPase) and a vacuolar $Na^+/H^+$ antiporter in leaf cells. As described herein, the plant components involved in the intracellular detoxification system have been identified by complementing salt-sensitive mutants of the budding yeast *Saccharomyces cerevisiae*. As also described herein, *Arabidopsis thaliana* has been used as a host model plant to demonstrate that overexpression of these genes results in salt tolerance in the plant.

Accordingly, the present invention is directed to transgenic plants which are tolerant to one or more salts. As used herein, the term "salt" refers to any salt, such as NaCl, KCl, and/or $CaCl_2$. In one embodiment, the transgenic plants of the present invention comprise one or more plant cells transformed with exogenous nucleic acid which alters expression of vacuolar pyrophosphatase in the plant. Any suitable vacuolar pyrophosphatase, several of which have been cloned, can be used in the compositions and methods of the present invention (e.g., Sarafian, V., et al., *Proc. Natl. Acad. Sci., USA*, 89:1775-1779 (1992); Lerchl, J., et al., *Plant Molec. Biol.*, 29: 833-840 (1995); Kim, Y., et al., *Plant Physiol.*, 106:375-382 (1994)). The teachings of Sarafian, V., et al., *Proc. Natl. Acad. Sci., USA*, 89:1775-1779 (1992), Lerchl, J., et al., *Plant Molec. Biol.*, 29: 833-840 (1995), and Kim, Y., et al., *Plant Physiol.*, 106:375-382 (1994), are incorporated by reference herein in their entirety. Sequences of *Arabidopsis* vacuolar pyrophosphatase cDNA (SEQ ID NO:6) and its encoded protein (AVP1; SEQ ID NO:7), both of which were disclosed in Sarafian, V., et al., *Proc. Natl. Acad. Sci., USA*, 89:1775-1779 (1992), are shown in FIG. 4. As used herein, nucleic acid which "alters expression of vacuolar pyrophosphatase" includes nucleic acid which enhances (promotes) or inhibits expression of vacuolar pyrophosphatase in the transgenic plant. In a particular embodiment, the present invention relates to a transgenic plant which is tolerant to salt comprising an exogenous nucleic acid construct which is designed to overexpress AVP1 (Sarafian, V., et al., *Proc. Natl. Acad. Sci., USA*, 89:1775-1779 (1992)) or designed to downregulate endogenous vacuolar pyrophosphatase. The present invention also encompasses transgenic plants which grow in a concentration of salt that inhibits growth of a corresponding non-transgenic plant. Transgenic progeny of the transgenic plants, seeds produced by the transgenic plant and progeny transgenic plants grown from the transgenic seed are also the subject of the present invention. Also described herein are plant cells comprising exogenous nucleic acid which alters expression of vacuolar pyrophosphatase in the plant cell.

Any suitable nucleic acid molecule which alters expression of vacuolar pyrophosphatase in the plant can be used to transform the transgenic plants in accordance with the present invention. Exogenous nucleic acid is a nucleic acid from a source other than the plant cell into which it is introduced or into a plant or plant part from which the transgenic part was produced. The exogenous nucleic acid used for transformation can be RNA or DNA, (e.g., cDNA, genomic DNA). In addition, the exogenous nucleic acid can be circular or linear, double-stranded or single-stranded molecules. Single-stranded nucleic acid can be the sense strand or the anti-sense strand.

The exogenous nucleic acid can comprise nucleic acid that encodes a vacuolar pyrophosphatase protein (an exogenous vacuolar pyrophosphatase), such as AVP1, a functional portion thereof (peptide, polypeptide), or a homologue thereof, and/or nucleic acid that alters (enhances, inhibits) expression of the endogenous vacuolar pyrophosphatase of the plant into which the exogenous nucleic acid is introduced. As used herein a "functional portion" of a nucleic acid that encodes a vacuolar pyrophosphatase protein is a portion of the nucleic acid that encodes a protein or polypeptide which retains a function characteristic of a vacuolar pyrophosphatase protein. In a particular embodiment, the nucleic acid encodes AVP1, a functional portion or a homologue thereof.

Nucleic acid that alters (enhances, inhibits) expression of the endogenous vacuolar pyrophosphatase of the plant into which the exogenous nucleic acid is introduced includes regulatory sequences (e.g., inducible, constitutive) which function in plants and antisense nucleic acid. Examples of regulatory sequences include promoters, enhancers and/or suppressors of vacuolar pyrophosphatase. The nucleic acid can also include, for example, polyadenylation site, reporter gene and/or intron sequences and the like whose presence may not be necessary for function or expression of the nucleic acid but can provide improved expression and/or function of the nucleic acid by affecting, for example, transcription and/or stability (e.g., of mRNA). Such elements can be included in the nucleic acid molecule to obtain optimal performance of the nucleic acid.

The nucleic acid for use in the present invention can be obtained from a variety sources using known methods. For example, the nucleic acid encoding a vacuolar pyrophosphatase (e.g., AVP1) for use in the present invention can be derived from a natural source, such as tobacco, bacteria, tomato or corn. In one embodiment, the nucleic acid encodes a vacuolar pyrophosphatase that corresponds to a wild type of the transgenic plant. In another embodiment, the nucleic acid encodes a vacuolar pyrophosphatase that does not correspond to a wild type of the transgenic plant. Nucleic acid that alters (enhances, inhibits) expression of the endogenous vacuolar pyrophosphatase of the plant into which the exogenous nucleic acid is introduced (e.g., regulatory sequence) can also be chemically synthesized, recombinantly produced and/or obtained from commercial sources.

A variety of methods for introducing the nucleic acid of the present invention into plants are known to those of skill in the art. For example, Agrobacterium-mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. The exogenous nucleic acid can be introduced into any suitable cell(s) of the plant, such a root cell(s), stem cell(s) and/or leaf cell(s) of the plant.

In one embodiment, a construct comprising a vacuolar pyrophosphatase gene operably linked to a promoter designed to overexpress the vacuolar pyrophosphatase (e.g., an expression cassette) or a construct designed to downregulate endogenous pyrophosphatase is used to produce the transgenic plants of the present invention. As used herein the term "overexpression" refers to greater expression/activity than occurs in the absence of the construct. In a particular embodiment, a construct comprising an AVP1 gene operably linked to a chimeric promoter designed to overexpress the AVP1 or designed to downregulate endogenous pyrophosphatase is used to produce the transgenic plants of the present invention. More particularly, the present invention relates to a construct wherein the AVP1 gene is operably linked to a double tandem enhancer of a 35S promoter.

Any suitable plant can be used to produce the transgenic plants of the present invention. For example, tomato, corn, tobacco, rice, sorghum, cucumber, lettuce, turf grass, ornamental (e.g., larger flowers, larger leaves) and legume plants can be transformed as described herein to produce the transgenic plants of the present invention. In addition, the transgenic plants of the present invention can be grown in any medium which supports plant growth such as soil or water (hydroponically).

The present invention also encompasses methods of making a transgenic plant which is tolerant to salt. In one embodiment, the method comprises introducing into one or more cells of a plant exogenous nucleic acid which alters expression of vacuolar pyrophosphatase in the plant to yield transformed cells in the plant, thereby producing a transgenic plant which is tolerant to salt. In another embodiment, the method comprises introducing into one or more cells of a plant a nucleic acid construct which is designed to overexpress AVP1 to yield transformed cells, thereby producing a transgenic plant which is tolerant to salt. The methods of making a transgenic plant can further comprise regenerating plants from the transformed cells to yield transgenic plants and selecting a transgenic plant which is tolerant to salt. The transgenic plants produced by these methods are also encompassed by the present invention.

The transgenic plants of the present invention are useful for a variety of purposes. As described herein, the plant components involved in an intracellular cation detoxification system have been identified by complementing salt-sensitive mutants of the budding yeast Saccharomyces cerevisiae. The present invention relates to a method of bioremediating soil comprising growing one or more transgenic plants and/or progeny thereof in the soil, wherein the transgenic plants and/or progeny thereof comprise exogenous nucleic acid which alters expression of vacuolar pyrophosphatase in the plant. In another embodiment, the present invention relates to a method of removing cations (e.g., monvalent and/or divalent cations) from a medium which can support plant growth (e.g., soil, water) comprising growing one or more transgenic plants and/or progeny thereof in the medium, wherein the transgenic plants and/or progeny thereof comprise exogenous nucleic acid which alters expression of vacuolar pyrophosphatase in the plant. For example, the method can be used to remove sodium (Na), lead (Pb), manganese (Mn) and/or calcium (Ca) ions from a medium which supports plant growth.

Furthermore, it has been shown herein that the transgenic plants of the present invention are larger than the corresponding wild type plants (Example 3). Thus, the present invention provides for a method of increasing the yield of a plant comprising introducing into one or more cells of a plant nucleic acid which alters expression of vacuolar pyrophosphatase in the plant to yield transformed cells, thereby increasing the yield of the plant. The present invention also relates to a method of making a plant which is larger than its corresponding wild type plant comprising introducing into one or more cells of a plant nucleic acid which alters expression of vacuolar pyrophosphatase in the plant to yield transformed cells, thereby producing a transgenic plant which is larger than its corresponding wild type plant. The method can further comprise regenerating plants from the transformed cells to yield transgenic plants and selecting a transgenic plant which is larger than its corresponding wild type plant, thereby producing a transgenic plant which is larger than its corresponding wild type plant. Also encompassed by the present invention is a method of making a transgenic plant (e.g., an ornamental plant) having increased flower size compared to its corresponding wild type plant comprising introducing into one or more cells of a plant nucleic acid which alters expression of vacuolar pyrophosphatase in the plant to yield transformed cells, thereby producing a transgenic plant having increased flower size compared to its corresponding wild type plant.

The present invention also provides for a method of producing a transgenic plant which grows in salt water comprising introducing into one or more cells of a plant nucleic acid which alters expression of vacuolar pyrophosphatase in the plant to yield transformed cells, thereby producing a transgenic plant which grows in salt water. As used herein, "salt water" includes water characterized by the presence of salt, and preferably wherein the concentration of salt in the water is from about 0.2M to about 0.4M. In one embodiment, salt water refers to sea water.

The transgenic plants of the present invention can also be used to produce double transgenic plants which are tolerant to salt wherein a plant is transformed with exogenous nucleic acid which alters expression of a vacuolar phosphatase and exogenous nucleic acid which alters expression of another protein involved in sequestration of cations and/or detoxification in plants. In one embodiment, the present invention relates to a double transgenic plant which is tolerant to salt comprising one or more plant cells transformed with exogenous nucleic acid which alters expression of a vacuolar pyrophosphatase and an $Na^+/H^+$ antiporter in the plant. In one embodiment, the vacuolar pyrophosphatase is AVP1 or a homologue thereof and the $Na^+/H^+$ antiporter is AtNHX1 or a homologue thereof. The present invention further relates to a transgenic progeny of the double transgenic plant, as well as seeds produced by the transgenic plant and a progeny transgenic plant grown from the seed.

Figure 3A:
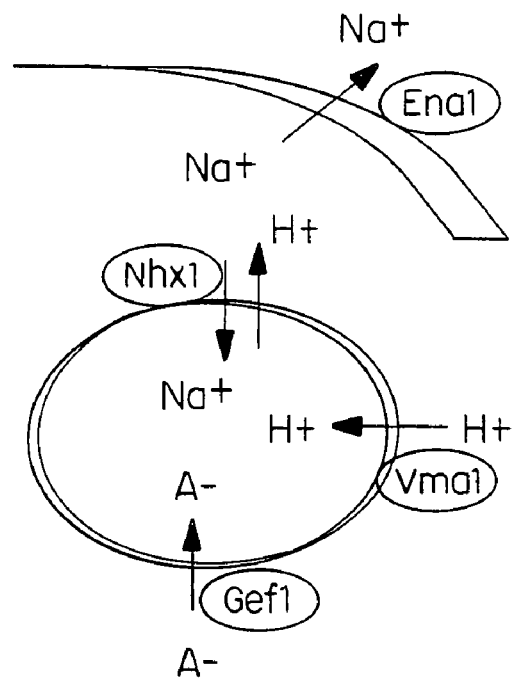
FIG. 3A is a schematic representation of a working model of the transporters involved in sodium sequestration at the yeast prevacuolar compartment; Nhx1 ($Na^+/H^+$ antiporter), Vma1 (vacuolar membrane $H^+$-ATPAse), Gef1 (yeast CLC chloride channel), Ena1 (plasma membrane $Na^+$-ATPase).
Figure 3B:
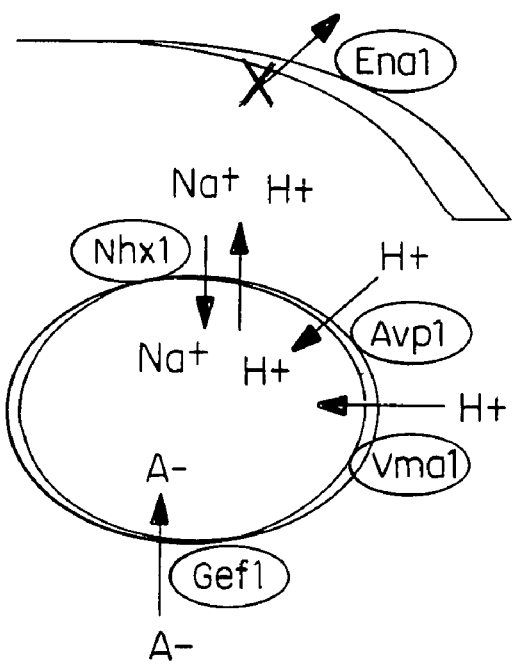
FIG. 3B is a schematic representation of a working model of the transporters involved in sodium sequestration at the yeast prevacuolar compartment shown in FIG. 3A, which also includes Avp1 (*A. thaliana* vacuolar pyrophosphate-energized proton pump).

Investigation of the role of intracellular organelles in cation homeostasis via the identification and manipulation of key transporters is described herein. Most of these intracellular organelles, including clathrin-coated vesicles, endosomes, Golgi membranes and vacuoles have acidic interiors (Xie, X. S., et al., *J. Biol. Chem.*, 264:18870-18873 (1989)). This acidification is mediated by a proton-translocating electrogenic ATPase and in plant vacuoles also via a pyrophosphate-driven proton pump V-PPase (Davies, J. M., et al., The Bioenergetics of Vacuolar H+ Pumps. In: Leigh R. A., Sanders, D., (eds) *The Plant Vacuole*, pp. 340-363, Academic Press, San Diego (1997); Zhen, R. G., et al., "The Molecular and Biochemical Basis of Pyrophosphate-Energized Proton Translocation at the Vacuolar Membrane Academic Press Limited (1997)). There exists a requirement of anion transport to maintain net electroneutrality (al-Awqati, A., *Curr. Opin. Cell. Biol.*, 7:504-508 (1995)). The yeast member of the CLC voltage-gated chloride channel superfamily, Gef1, is required for copper loading in late-Golgi vesicles and for cation sequestration in the prevacuolar compartment in yeast (Gaxiola, R. A., et al., *Proc. Natl. Acad. Sci. USA*, 95:4046-4050 (1998); Gaxiola, R. A., et al., *Proc. Natl. Acad. Sci. USA*, 96:1480-1485 (1999); Example 1). Furthermore, it has been shown that the defects of gef1 mutants can be suppressed by the introduction of the prototype member of the CLC superfamily, the *Torpedo marmorata* CLC-0 or by the introduction of *Arabidobsis thaliana* CLC-c and CLC-d chloride channel genes (Hechenberger, M., et al., *J. Biol. Chem.*, 271:33632-33638 (1996); Gaxiola, R. A., et al., *Proc. Natl. Acad. Sci. USA*, 95:4046-4050 (1998)). While not wishing to be bound by theory, two observations led to the proposal of a model for $Na^+$ sequestration in yeast described herein (FIGS. 3A and 3B). First, gef1 mutants are sensitive to high NaCl concentrations. Second, the $Na^+/H^+$ exchanger Nhx1 localized to the prevacuolar compartment (Nass, R., et al., *J. Biol. Chem.*, 273:21054-21060 (1998)). This model posits that $Na^+$ sequestration by Nhx1 depends on the vacuolar $H^+$-ATPase and Gef1, the chloride channel. Gef1-mediated anion influx allows the establishment by the vacuolar $H^+$-ATPase of a proton gradient sufficient in magnitude to drive the uphill accumulation of $Na^+$ via $Na^+/H^+$ exchange.

This model is entirely consistent with the physiological data on the role of the vacuole in cation detoxification in higher plants. As described in Example 1, to test this sequestration model, mutant yeast strains (ena1) lacking the plasma membrane sodium efflux pump, which therefore must rely on the internal detoxification system in order to grow on high salt, were constructed. In theory, increasing the influx of protons into the postulated endosomal compartment should improve $Na^+$ sequestration via the Nhx1 exchanger. In order to increase the $H^+$ availability the *A. thaliana* gain-of-function mutant gene AVP1-D that codes for the vacuolar pyrophosphate-energized proton pump was expressed (FIG. 3B) (Zhen, R. G., et al, *J. Biol. Chem.*, 272:22340-22348 (1997)). This plant pump expressed in yeast restored the $Na^+$ resistance of the test strain, but only if the strain had functional NHX1 and GEF1 genes. Furthermore, Gef1p and Nhx1p colocalize within a common organelle, the prevacuolar compartment (Gaxiola, R. A., et al., *Proc. Natl. Acad. Sci. USA*, 96:1480-1485 (1999)). These results strongly support the model in FIGS. 3A and 3B and indicate that the yeast prevacuolar compartment can be used to identify the elusive plant transporters involved intracellular sodium detoxification.

Yeast and plant cells share pathways and signals for the trafficking of vesicles from the Golgi network to the vacuole (Neuhaus, J. M., et al., *Plant Mol. Biol.*, 38:127-144 (1998); (Paris, N., et al., *Plant Physiol.*, 115:29-39 (1997); Sato, M. H., et al., *J. Biol. Chem.*, 272:24530-24535 (1997); Vitale, A. V., et al., *Trends Plant Sci.*, 4:148-154 (1999)). As shown herein, intracellular $Na^+$ detoxification in yeast requires functional $Na^+/H^+$ exchanger (Nhx1) and chloride channel (Gef1), and they colocalize to a prevacuolar compartment (Gaxiola, R. A., et al., *Proc. Natl. Acad. Sci. USA*, 96:1480-1485 (1999)). As described in Example 1, to further test the utility of this system, an *Arabidopsis thaliana* homologue of the yeast NHX1 gene (AtNHX1) was cloned and its function in the nhx 1 yeast mutant was tested. The AtNHX1 gene was able to suppress partially the cation sensitivity phenotypes of nhx1 mutants. Further support for the role of the *Arabidopsis* AtNHX1 gene in salt homeostasis came from the observation that its expression is induced in salt-stressed plants (Gaxiola, R. A., et al., *Proc. Natl. Acad. Sci. USA*, 96:1480-1485 (1999)). A recent report shows that the overexpression of AtNHX1 gene in transgenic *Arabidopsis thaliana* promotes sustained growth in soil watered with 200 mM NaCl plys ⅛ M.S. salts under short-day cycle conditions (Apse, M., et al., *Science*, 285:1256-1258 (1999)). It is worth noting that every addition of ⅛ M.S. salts provides 2.5 mM potassium reducing the stringency of the NaCl stress, and that a short-day cycle reduces oxidative stress. As described in Example 2, transgenic plants that overexpress the AtNHX1 were generated (35SAtNHX1 transgenics).

In plants, most of the transport processes are energized by the primary translocation of protons. $H^+$-translocating pumps located at the plasma membrane and tonoplast translocated H+ from the cytosol to extracellular and vacuolar compartments, respectively (Rea, P. A., et al., Tonoplast Adenosine Triphosphate and inorganic Pyrophosphatase. In: *Methods Plant Biochem.*, pp. 385-405, Academic Press Limited, London (1990)). The plant tonoplast contains two H+-translocating pumps; the V-ATPase and the inorganic pyrophosphatase or V-PPase. Their action results in luminial acidification and the establishment of a H+ electrochemical potential gradient across the tonoplast (Davies, J. M., et al., The Bioenergetics of Vacuolar H+ Pumps. In: *Plant Vacuole*, pp. 340-363, Leigh, R. A., Sanders, D. (eds.), Academic Press, San Diego (1997)). The vacuolar membrane is implicated in a broad spectrum of physiological processes that include cytosolic pH stasis, compartmentation of regulatory $Ca^{2+}$, sequestration of toxic ions such as $Na^+$, turgor regulation, and nutrient storage and retrieval. The vacuole constitute 40 to 99% of the total intracellular volume of a mature plant cell. The vacuolar proton pumping pyrophosphatase is a universal and abundant component of plant tonoplast capable of generating a steady-state transtonoplast H+ electrochemical potential similar or greater than the one generated by the V-ATPase (Rea, P. A., et al., Tonoplast Adenosine Triphosphate and Inorganic Pyrophosphatase. In: *Methods Plant Biochem.*, pp. 385-405, Academic Press Limited, London (1990)). Pyrophosphate (PPi) is a by-product in the activation or polymerization steps of a wide range of biosynthetic pathways and in plants serves as an alternative energy donor to ATP for sucrose mobilization via sucrose synthase, for glycolysis via PPi: fructose-6-phosphate phosphotransferase and for tonoplast energisation via the vacuolar proton pumping pyrophosphatase (Stitt, M., *Bot. Acta* 111:167-175 (1998)).

As described in Example 1, the overexpression of the *A. Thaliana* gain-of-function mutant gene AVP1-D increases the intracellular detoxification capability in yeast (Gaxiola, R. A., et al., *Proc. Natl. Acad. Sci. USA*, 96:1480-1485 (1999)). The rationale behind this approach is that an increased influx of H+ into the vacuolar compartment should improve $Na^+$ sequestration via the Nhx1 exchanger. As described in Example 3, in order to test this hypothesis in plants, a transgenic *Arabidopsis thaliana* plant was engineered to overexpress the AVP1 wild-type gene using the double tandem enhancer of the 35S promoter (Topfer, R., et al., *Nucl. Acid Res.*, 15:5890 (1987)). AVP1 encodes the pyrophosphate-energized vacuolar membrane proton pump from *Arabidopsis* (Sarafian, V., et al., *Proc. Natl., Acad. Sci., USA*, 89:1775-1779 (1992)). Previous investigations suggest that the AVP1 gene is present in a single copy in the genome of *Arabidopsis* (Kim, Y., et al., *Plant Physiol.*, 106:375-382 (1994)), however, a sequence homologous, but not identical, to AVP1 on chromosome one has been tentatively designated as ORF F9K20.2 on BAC F9K20 by the Arabidopsis Genome Initiative (AGI).

Five different lines of 35SAVP1 plants showed an enhanced salt tolerance as compared to wild-type plants in the T2 stage. However, the most dramatic phenotype was apparent in the homozygous T3 plants. These transgenic plants are larger than wild-type plants. Furthermore, homozygous 35SAVP1 plants show sustained growth in the presence of 250 mM NaCl plus ⅛ M.S. salts when grown in a 24 hours light regimen. Interestingly, when 35SAVP1 plants were grown under short-day cycle conditions sustained growth in the presence of 300 mM NaCl plus ⅛ M.S. salts was observed.

Hydroponic culture increases plant growth and provides stress-free root and shoot material (Gibeaut, D. M., et al., *Plant Physiol.*, 317-319 (1997)). Another important advantage of hydrophonic culture is that we can alter the ionic composition in a more accurate manner than in soil. These advantages could be important for the physiological studies of salt stress. As described in Example 4, wild type and 35SAVP1 transgenic plants were grown hydroponically. Under such conditions the size differences in root, leaves and stems among wild type and 35SAVP1 transgenic plants are dramatic. To learn about the salt tolerance of these plants under hydroponic conditions, NaCl concentration were increased stepwise by 50 mM every 4 days (Apse, M., et al., *Science*, 285:1256-1258 (1999)). 35SAVP1 transgenic plants appear healthy in the presence of 200 mM NaCl while wild type controls show severe deleterious effects in their leaves and stems.

Genetic engineering promises to transform modern agriculture. Salinization of soil due to irrigation has rendered much land unusable for crop production. Described herein is a strategy using genetic and molecular biological approaches to improve the intracellular $Na^+$ detoxification capabilities of crops. The fact that genetically engineered *Arabidopsis thaliana* plants that overexpress either AVP1 (the pyrophosphate-energized vacuolar membrane proton pump, this work) or AtNHX1 (the $Na^+/H^+$ antiporter, (Apse, M., et al., *Science*, 285:1256-1258 (1999)) and this work) are capable of growing in the presence of 200 mM NaCl strongly supports the strategy described herein. It is likely that a double transgenic plant will show a further enhanced salt-tolerant phenotype. Furthermore, it is expected that these *Arabidopsis thaliana* transporters or their counterparts will be able to perform similar function in important agricultural crops. The increased size of $^{35}S$ AVP1 *Arabidopsis* transgenic plants also contribute to future food security, namely potential yield increases in genetically engineered crops.

EXEMPLIFICATION

Example 1

The *Arabidopsis Thaliana* Proton Transporters, AtNhx1 and Avp1, can Function in Cation Detoxification in Yeast Materials and Methods Yeast strains and Plasmids. All strains used are isogenic to W303 (ura3-1-can1-100 leu2-3, 112trp1-1 his3-11, (Gaxiola, R. A., et al., *EMBO J.*, 11:3157-3164 (1992)). Plasmids pRG52 (Δgef1::HIS3) (Gaxiola, R. A., et al., *Proc. Natl. Acad. Sci. USA*, 95:4046-4050 (1998)) and pRG197 (Δnhx1::HIS3) were used to construct the deletions of GEF1 and NHX1 genes, yielding strains RGY85 and RGY296, respectively. The enal::HIS3 mutant was obtained from Fink Lab collection (L5709). Transformation was performed by using the lithium acetate method (Gietz, D., et al., *Nucleic Acids Res.*, 20:1425 (1992)). Double mutants RGY324 (gef1::HIS3 enal::HIS3), RGY326 (nhx1::HIS3 enal::HIS3), and RGY343 (gef1::HIS3 nhx1::HIS3) were obtained by crossing the single-mutant strains. Double mutants were identified among the meiotic progeny by scoring for the phenotypes associated with each of the single mutants. Sporulation, tetrad dissection, and mating types were scored as described (Guthrie C. and Fink, G. R., *Guide to Yeast Genetics and Molecular Biology* (Academic, San Diego (1991)). Cells were grown in YPD (1% yeast/2% peptone/2% dextrose; Difco), YPGAL (1% yeast/2% peptone/2% galactose; Difco), SD (Difco; Synthetic medium with 2% Dextrose), or APG (APG is a synthetic minimal medium containing 10 mM arginine, 8 mM phosphoric acid, 2% glucose, 2 mM $MgSO_4$, 1 mM KCl, 0.2 mM $CaCl_2$, and trace minerals and vitamins) (Rodriguez- Navarro, A. and Ramos, J., *J. Bacteriol.*, 159:940-945 (1984)). MnCl$_2$ (Sigma), tetramethylammonium chloride (Sigma), NaCl (Sigma), or hygromycin-B (Sigma were added as indicated.

Wild type, L5709 (ena1::HIS3), RGY324 (gef1::HIS3 ena1::HIS3), and RGY326 (nhx1::HIS3 ena1::HIS3) strains were transformed with pYES2 vector (Invitrogen) and plasmid pYES2-AVP1-E229D described in ref. Zhen, R. G., et al., *J. Biol. Chem.*, 272:22340-22348 (1997). The strain RGY343 (gef1::HIS3 nhx1::HIS3), used for histochemical analysis, was transformed with pRG151 (GEF1-GFP) (Gaxiola, R. A., et al. *Proc. Natl. Acad. Sci. USA*, 95:4046-4050 (1998)) and with pRIN73 [NHX1-(HA)$_3$] (Nass, R., and Rao, R., *J. Biol. Chem.*, 273:21054-21060 (1998)).

Wild-type and RGY296 (nhx1::HIS3) strains were transformed with vector pAD4 (Ballester, R., et al., *Cell*, 59:681-686 (1989)). RGY296 (nhx1::HIS3) was transformed with pRG308 (ADH1::AtNHX1) (see Cloning of AtNHX1).

Determination of Intracellular Sodium and Potassium content. Cells were grown overnight in SD-ura medium (Difco; synthetic medium with 2% dextrose without uracil). YPGAL (1% yeast extract/2% peptone/2% galactose; Difco) media was inoculated with the overnight stocks and grow to an A$_{600}$ of 0.6. At this OD, NaCl was added to a final concentration of 0.7 M. The cells incubated for 6 h, harvested by centrifugation, washed two times with 1.1 M sorbitol and 20 mM MgCl$_2$, and entracted with water for 30 min at 95° C. The amount of Na$^+$ and K$^+$ in cells was determined at the University of Georgia Chemical Analysis Laboratory by an Inductively Coupled Plasina-MS Intracellular cation concentrations were estimated as described (Gaxiola, R. A., et al., *EMBO J.*, 11:3157-3164 (1992)) by using the intracellular water value calculated for cells grown in 1M NaCl.

Immunofluorescence. The strain RGY343 (gef1::HIS3 nhx1::HIS3) was grown in SD-ura, -leu medium (Difco; synthetic medium with 2% dextrose without uracil and leucin) to mid-logarithmic phase, 0.1 mg/ml hygromycin B was added, and the culture was incubated for 1 h at 30° C. Cells were fixed with 3.7% formaldehyde (Sigma) for 45 min at room temperature without agitation. Spheroplast formation, permeablization, washing, and antibody incubation was performed as described (Pringle, J., et al., in *Immunofluorescence Methods for Yeast*, eds. Guthrie, C. And Fink, G. F. (Academic, Sand Diego), Vol. 194 pp. 565-602 (1991)). MAB HA11 used as first antibody was from Babco (Richmond, Calif.). Cy3-conjugated goat antimouse IgG was from Jackson Immunoresearch. 4',6-Diamidino-2-phenylindole (Sigma) was added to mounting medium to stain mitochondrial and nuclear DNA.

Subcellular Fractionation and Western Analysis. The strain RGY343 (gef1::HIS3 nhx1::HIS3) was grown in APG medium (pH 7.0), and lysates fractioned on a 10-step sucrose density gradient as described (Nass, R. and Rao, R., *J. Biol. Chem.*, 273:21054-21060 (1998)). Aliquots of individual fractions (100 μg) were subjected to SDS/PAGE and transferred to nitrocellulose as described (Nass, R. and Rao, R., *J. Biol. Chem.*, 273:21054-21060 (1998)). Western blots were probed with monoclonal anti-GFP (green fluorescent protein) antibody (1:10,000 dilution; CLONTECH), anti-hemagglutinin antibody (1:10,000 dilution: Boehringer Mannheim), and peroxidase-coupled goat anti-mouse antibody (1:5,000); and developed by using the ECL enhanced chemiluminescence system (Amersham Pharmacia).

Plant Strains, Growth conditions and RNA Preparation. *A. thaliana* plants (ecotype Columbia) were grown aseptically on unsupplemented plant nutrient agar without sucrose (Haughn, G. W. and Somerville, C., *Mol. Gen. Genet.*, 204: 430-434 (1986)) for 15 days at 19° C. and under continuous illumination. NaCl or KCl was added to a final concentration of 250 mM, and the plants were incubated for 6 h. Total RNA from tissue of salt-treated and untreated plants was isolated (Niyogi, K. K. and Fink, G. R., *Plant Cell*, 4:721-733 (1992)), Hybond-N (Amersham) membranes were hybridized with a $^{32}$P-Labeled DNA probe from plasmid pRG308. Hybridization was performed at 65° C. overnight. Washes were performed at 65° C. with 0.2% standard saline citrate (SSC)/0.1% SDS (Ausebel, F., et al., *Curr. Protocols in Mol. Biol.* (Wiley, NY) (1988)). 18S probe was used as loading control (Unfried, I., et al., *Nucleic Acids Res.*, 17:7513 (1989)). MACBAS 2.4 program was used to quantify the relative amount of RNA.

Cloning of AtNHX1. AtNHX1 was cloned from a phage cDNA library of *A. thaliana* (Kieber, J. J., et al., *Cell*, 72:427-441 (1993)) (obtained from the Arabidopsis Biological Resource Center) by probing with an expressed sequence tag (*Arabidopsis* Biological Resources Center, DNA Stock Center) containing a partial clone. A full-length clone (2.1 kB) was ligated into vector pSK2 (Stratagene) at the NotI sit, generating plasmid pRG293. The AtNHX1 ORF was amplified via PCR by using pRG293 as template and GGCCCGG-GATGGATTCTCTAGTGTCGAAACTGCCTTCG (SEQ ID NO: 5) (italicized bases correspond to nucleotides 1-30 of the ORF) and T7 oligonucleotides. The PCR product was then digested with XbaI and SalI and ligated into pAD4 vector generating plasmid pRG308. The AtNHX1 ORF was sequenced to verify the fidelity of the PCR product. The full-length sequence is longer than the ORF reported by the Arabidopsis Genome Initiative (A TM021B04.4), and has been deposited in GenBank (accession no. AF106324).

Results

The *Arabidopsis* Vacuolar H$^+$-Pyrophosphatase (Avp1) Confers Salt Tolerance to Yeast ena1 Mutants. To determine the components of the intracellular system required for sodium detoxification, an ena1 mutant that lacks the plasma membrane sodium efflux pump and therefore must rely on the internal detoxification system to overcome sodium toxicity was used. Growth of the ena1 strain is sensitive to low concentrations of sodium (200 mM), concentrations that do not inhibit the growth of wild-type strains. The sequestration model (Nass, R. and Rao, R., *J. Biol. Chem.*, 273:21054-21060 (1998) and, Gaxiola, R. A., et al., *Proc. Natl. Acad. Sci. USA*, 95:4046-4050 (1998)) predicts that the ena1 strain would become salt tolerant if one could enhance the availability of protons in the postulated endosomal compartment. With increased influx of protons, cytoplasmic Na$^+$ would be sequestered via the Nhx1 exchanger. The yeast vacuolar ATPase is a multisubunit protein, so it is difficult to increase its activity by overexpressing any one of its subunits. However, it is possible to increase the influx of protons by expressing the *A. thaliana* AVP1 gene in yeast. This gene encodes a single polypeptide that, when expressed in yeast, is capable of pumping protons into the lumen of the vacuole (Kim, E. J., et al., *Proc. Natl. Acad. Sci. USA*, 91:6128-6132 (1994)). To ensure maximum activity of this proton pump, the E229D gain-of-function mutant of the AVP1 gene (AVP1-D) that has enhanced H$^+$ pumping capability was expressed (Zhen, R. G., et al., *J. Biol. Chem.*, 272:22340-22348 (1997)).

Overexpression of AVP1-D restored salt tolerance to salt-sensitive ena1 mutants. The restoration of salt tolerance to an ena1 strain by AVP1-D requires functional NHX1 and GEF1 genes: ena1nhx1 AVP1-D and ena1 gef1 AVP1-D strains are salt sensitive.

Figure 1B:
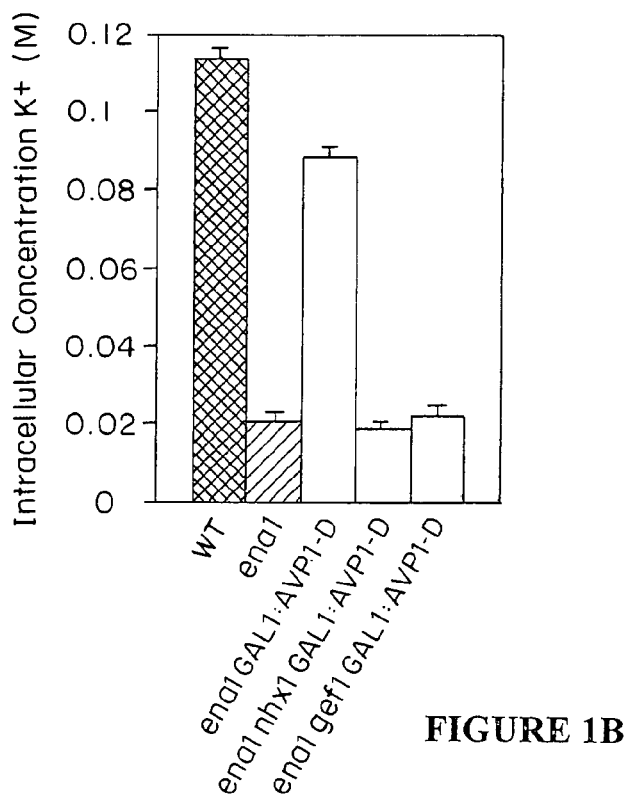

Expression of *Arabidopsis* vacuolar pyrophosphatase AVP1 in ena1 mutants: Vector pYES2 (Invitrogen) was introduced into wild-type, ena1, ena1 nhx1, and ena1 gef1 mutants. Plasmid pYes2-AVP1-D (Zhen, R. G., et al., *J. Biol. Chem.*, 272:22340-22348 (1997)) was introduced into ena1, ena1 nhx1, and ena1 gef1 mutants. Five-fold serial dilutions (starting at $10^5$ cells) of each strain were plated on YPGAL (1% yeast extract/2% peptone/2% galactose) with or without 0.5 M NaCl and incubated at 30° C. for 2 days. FIGS. 1A and 1B show intracellular concentrations of $Na^+$ and $K^+$. Exponentially growing cells (wild-type and ena1 transformed with pYES2 vector and ena1, ena1 nhx1, and ena1 gef1 mutants carrying pYes2-AVP1-D) were exposed to 0.7M NaCl or 6 hours. Total cell extracts were prepared (see Materials and Methods), and $Na^+$ and $K^+$ concentrations were determined. There is a consistent reduction in total cell $Na^+$ in the ena1 AVP-D strain. The reason for this reduction is unknown.

The intracellular $Na^+$ and $K^+$ contents of wild-type strains and of strains carrying various mutations affecting sodium tolerance were determined after 6 h of exposure to media supplemented with 0.7 M NaCl (FIGS. 1A and 1B). The intracellular $Na^+$ content in the ena1 mutant is 8-fold higher than in the wild-type strain. The ena1 AVP-D strain is salt-resistant, even though its intracellular $Na^+$ content is 4-fold higher than that of the wild type. In ena1 AVPI-D strains lacking either gef1 or nhx1 (i.e., ena1 gef1 or ena1 nhx1), the $Na^+$ content is not reduced to the extent that it is in GEF1 NHX1 strain. Taken together, the genetic and physiological data are consistent with the model that Nhx1, Gef1 and Avp1 cooperate to sequester sodium internally.

The intracellular $K^+$ content correlates with salt tolerance and is inversely correlated with the $Na^+$ content of our strains (FIG. 1B). The wild-type $K^+$ concentration is ≈100 mM but is reduced to 20 mM in the ena1 mutant. Interestingly, in an ena1 strain that overexpresses the AVP1-D gene, the intracellular concentration of $K^+$ is restored almost to wild-type levels (FIG. 1B). However, AVP1-D overexpression fails to restore wild-type levels of intracellular potassium unless both NHx1 and GEF1 are functional (see the double mutants ena1 nhx1 or ena1 gef1 in FIG. 1B).

The NHX1 and GEF1 genes, which have been identified as important in sodium detoxification, are also required for the detoxification of other cations. Growth of gef1 and nhx1 mutants in the presence of toxic cations: Five-fold serial dilutions (starting at $10^5$ cells) of the indicated strains were grown at 30° C. for 2 days on YPD (1% yeast extract/2% peptone/2% dextrose) with the addition of either 3 mM $MnCl_2$, 0.45 M tetramethylammonium (TMA), or 0.05 mg/ml hygromycin B (HYG) as indicated.

For example, gef1 mutants are sensitive to 3 mM $MnCl_2$, 0.45 M tetramethylammonium chloride and to 0.05 μg/ml hygromycin-B. The nhx1 mutant is also sensitive to tetramethylammonium chloride and hygromycin. The extreme sensitivity of the nhx1 mutant to hygromycin provides an important tool for assaying nhx1 function.

Gef1p and Nhx1p Colocalize. The sequestration model postulates not only a functional connection between the anion channel Gef1 and sodium exchanger Nhx1 but also predicts that these two proteins colocalize within a common compartment. Because previous studies indicated that Nhx1 localizes to a prevacuolar compartment (Nass, R. and Rao, R., *J. Biol. Chem.*, 273:21054-21060 (1998)), two types of experiments were performed to determine whether Gef1 and Nhx1 proteins colocalize to this compartment.

Distribution of fluorescence and immunodetection of subcellular fractions in gef1 nhx1 cells transformed with two constructs: a GEF1-GFP fusion and a NHX1-(HA)$_3$-tagged fusion were determined. The strain RGY419 (gef1 nhx1) was transformed with plasmids pRG151; GEF1-GFP and pRIN73; NHX1-(HA)$_3$. Transformants were grown in SD (Difco; synthetic medium with 2% dextrose). When the cells reached $OD_{600}$=0.5, hygromycin B (Sigma) was added to a final concentration of 0.1 mg/ml and the cells were incubated for 40 min at 30° C. Cells were fixed and stained with antibodies to HA epitope and 4',6-diamidino-2-phenylindole (DAPI). Cells were viewed by charge-coupled device microscopy and optically sectioned by using a deconvolution algorithm (Scanalytics, Billerica, Mass.) (Kennedy, B. K., et al., *Cell*, 89:381-391 (1997)); (Bar=1 μm.).

It was found that hemagglutinin (HA)-tagged Nhx1 and Gef1-GFP fusion protein colocalize as shown via epifluorescence deconvolution microscopy (FIG. 3A). Persistence of signal coincidence on 90° rotation of the image further supports colocalization of the two transporter proteins in these cells.

The colocalization of Nhx1 (HA)$_3$ and GEF1-GFP is also supported by the comigration of the two proteins in sucrose density gradients of membrane preparations obtained from cells expressing the tagged proteins. The strain RGY419 (gef1 nhx1) transformed with plasmids pRG151; GEF1-GFP and pRIN73; NHX1-(HA)$_3$ was grown in APG medium (Rodriguez-Navarro, A. and Rea, P. A., J. Biol. Chem., 159:940-945 (1984)), converted to spheroplasts, lysed, and fractionated on a 10-step sucrose gradient (18-54%) as described (Sorin, A., et al, *J. Biol. Chem.*, 272:9895-9901 (1997) and Antebi, A. and Fink, G. R., *Mol. Biol. Cell*, 3:633-654 (1992)). Western blots showed the distribution of Gef1-GFP and Nhx1-HA (see Example 1, Materials and Methods).

The sedimentation behavior of the membrane fraction containing both proteins is consistent with that of a prevacuolar compartment (Nass, R. and Rao, R., *J. Biol. Chem.*, 273:21054-21060 (1998)). Gef1-GFP (but not Nhx1) is also present in Golgi fractions, consistent with previous studies (Gaxiola, R. A., et al., *Proc. Natl. Acad. Sci. USA*, 95:4046-4050 (1998), Schwappach, B., et al., *J. Biol. Chem.*, 273: 15110-15118 (1998)).

An *A. thaliana* Homologue of NHX1 Functions in Yeast. The yeast strain described herein provides an important tool for identifying genes that mediate salt tolerance in other organisms. To test the utility of this system, a sequence from *Arabidopsis* (See Materials and Methods) with very high homology to the *S. cerevisiae* NHX1 ORF was identified and used an expressed sequence tag (see Materials and Methods) to obtain a full-length clone of this *Arabidopsis* gene. An alignment of the amino acid sequences of Nhx1 homologues from *Arabidopsis* (AtNhx1), human (HsNhe6), and yeast (ScNhx1) reveals segments of amino acid identity and similarity within predicted transmembrane domains (FIG. 2). However, it is important to note that despite these relationships, neither the – nor the C-terminal regions of AtNhx1 and ScNhx1 show a high degree of homology (FIG. 2). A characteristic of mammalian $Na^+/H^+$ antiporters is their inhibition by amiloride. A putative amiloride binding site ($^{163}$DVF-FLFLLPPI$^{173}$) (SEQ ID NO: 4) has been defined via point mutants in the human NHE1 antiporter gene (Counillon, L., et al., *Proc. Natl. Acad. Sci. USA*, 90:4508-4512 (1993)). AtNhx1, HsNhe-6 and ScNhx1 have an almost identical sequence (FIG. 2). However, our attempts to inhibit the activity of either Nhx1 or AtNhx1 in yeast cultures with amiloride were unsuccessful.

The extreme sensitivity of yeast nhx1 mutants to hygromycin permitted the testing of whether the cloned *Arabidopsis* AtNHX1 ORF could provide $Na^+/H^+$ exchange function in yeast. Vector pAD4 (Ballester, R., et al., *Cell*, 59:681-686 (1989) was introduced into wild-type and nhx1 strains. Plasmid pRG308; ADH; AtNHX1 was introduced into nhx1 mutants as indicated. Five-fold serial dilutions (starting at 10⁵ cells) of the indicated strains were grown at 30° C. for 2 days on YPD (−) or on YPD supplemented with 0.05 mg/ml hygromycin (+). Serial dilutions of the same strains were grown on APG medium (see Materials and Methods) (−) or on APG supplemented with 0.4 M NaCl (Rodriguez-Navarro, A. and Ramos, J., *J. Bacteriol.*, 159:940-945 (1984).

The At NHX1 gene is capable of suppressing the hygromycin sensitivity of the nhx1 mutant. The AtNHX1 gene also suppressed the NaCl sensitivity of nhx1 mutant but only under conditions in which the $K^+$ availability was reduced. However, AtAHX1 was not capable of rescuing the $Na^+$-sensitive growth phenotype of the double mutant ena1 nhx1 overexpressing the AVP1-D gene.

Further support for the role of the *Arabidopsis* AtNHX1 gene in salt homeostasis came from an analysis of its expression in salt-stressed plants. Plants were grown for 15 days under standard conditions and then exposed for 6 h to either 250 mM NaCl or KCl. The NaCl stress increased AtNHX1 mRNA levels 4.2-fold, whereas KCl promoted only a 2.8-fold increase. This increase in mRNA level produced by sodium resembles that described for the yeast NHX1 gene (Nass, R. and Rao, R., *J. Biol. Chem.*, 273:21054-21060 (1998)). RNA tissue blot hybridized with AtNHX1. Ten micrograms of total RNA from 15-day old plants exposed to 250 mM NaCl or Kcl for 6 h and a control grown without salt was subjected to electrophoresis on a denaturing formaldehyde gel. The blot was hybridized with a probe internal to AtNHX1 ORF. An 18S ribosomal probe was used as a loading control.

Discussion

The studies described herein provide evidence for the importance of the prevacuolar pH for intracellular $Na^+$ sequestration in yeast. Overexpression of the plant $H^+$-pyrophosphatase (Avp1) confers salt tolerance to yeast only in those strains containing a functional chloride channel (Gef1) and the $Na^+/H^+$ exchanger (Nhx1).

These data support a model in which the Nhx1 $Na^+/H^+$ exchanger acts in concert with the vacuolar ATPase and the GEF1 anion channel to sequester cations in a prevacuolar compartment. Several studies suggest that the prevacuolar compartment may be derived both from the plasma membrane and the late Golgi. These vesicles are likely involved in the assembly of the vacuole or delivery of cargo to this organelle. It is reasonable to expect that these prevacuolar vesicles detoxify cations by sequestration, thereby lowering their concentrations in the cytoplasm and in other organelles.

The yeast system described herein permits the functional assessment of diverse heterologous proteins in salt tolerance: chloride channels, $H^+$ pumps, and $Na^+/H^+$ exchangers and other cation/$H^+$ exchangers or cation/bicarbonate symporters. The system is robust and flexible. The function of the *Arabidopsis* chloride channels (Gaxiola, R. A., et al., *Proc. Natl. Acad. Sci. USA*, 95:4046-4050 (1998), Hechenberger, M., et al., *J. Biol. Chem.*, 271:33632-33638 (1996)), $H^+$ pump, and $Na^+/H^+$ exchanger can be assayed in the corresponding yeast mutant. Despite the inability of At NHX1 to suppress all the phenotypes of the yeast nhx1 mutant, the fact that it suppresses some phenotypes, coupled with the DNA homology between AtNHX1 and yeast NHX1, indicates that the plant gene carries out a similar function to that of the yeast homologue. The observation that the AtNHX1 gene suppresses the sensitivity of the nhx1 mutant to hygromycin but provides only a weak $Na^+$ detoxification phenotype could be a consequence either of differential regulation of the transporters in the two organisms or of distinct cation transport selectivities.

The regulation of AtNHX1 by salt and the ability of the plant gene to suppress the yeast nhx1 mutant suggest that the mechanism by which cations are detoxified in yeast and plants may be similar. Indeed, previous work suggested that vacuolar sodium accumulation in salt-tolerant plants may be mediated by a tonoplast $Na^+/H^+$ antiporter that utilizes the proton-motive force generated by the vacuolar $H^+$-ATPase (V-ATPase) and/or $H^+$-translocating pyrophosphatase (V-PPase; refs. Barkla, B. J., et al., *Symp. Soc. Exp. Biol.*, 48:141-153 (1994), Zhen, R. G., et al., *The Molecular and Biochemical Basis of Pyrophosphate-Energized Proton Translocation at the Vacuolar Membrane* (Academic, San Diego), Kirsh, M, et al., *Plant Mol. Biol.*, 32:543-547 (1996)).

The finding described herein that both gef1 and nhx1 mutants are hypersensitive to hygromycin indicate that the level of resistance to hygromycin depends on the function of the vacuolar and prevacuolar organelles. Yeast mutants impaired in $K^+$ uptake (trk1) are hypersensitive to hygromycin (Madrid, R., et al., *J. Biol. Chem.*, 273:14838-14844 (1998)); reduced $K^+$ uptake hyperpolarizes the plasma membrane potential and drives the uptake of alkali cations such as hygromycin. Mutations that reduce the $H^+$ pumping activity of the plasma membrane $H^+$-ATPase, Pma1, depolarize the plasma membrane potential and confer resistance to hygromycin (McCusker, J. H., et al., *Mol. Cell. Biol.*, 7:4082-4088 (1987)). Thus, mutants such as gef1 or nhx1 that affect the pH or membrane potential of the vacuolar and prevacuolar compartments may be expected to affect hygromycin compartmentation.

Example 2

Transgenic Plants that Overexpress the AtNHX1

Transgenic plants that overexpress the AtNHX1 were generated using *Agrobacterium*-mediated plant transformation. The transgenic AtNHX1 was expressed using a double tandem enhancer of the 35S promoter of CaMV (Topfer, R., et al., *Nucl. Acid Res.*, 15:5890 (1987)). T3 transgenic plants are less affected than wild type controls when watered with 300 mM NaCl.

15 wild-type plants and 15 35SAtNHX1 transgenic were grown on a 12 hours-day cycle for 20 days. During this period plants were watered every 5 days with a diluted nutrient solution (⅛ M.S. salts). 200 mM NaCl was added to the watering solution at day 21 and at day 33 plants were watered with a nutrient solution containing 300 mM NaCl. Plants were photographed 10 days after the last NaCl treatment.

Example 3

Salt-Stressed Wild Type Plants and 35SAVP1 Transgenics

Transgenic plants that overexpress AVP1 were generated using *Agrobacterium*-mediated plant transformation. The transgenic AVP1 was expressed using a double tandem enhancer of the 35S promoter of CaMV (Topfer, R., et al., *Nucl. Acid Res.*, 15:5890 (1987)). 15 wild-type plants and 15 35SAVP1 transgenics were grown on a 24 hours-day cycle for 16 days. During this period plants were watered every 4 days with a diluted nutrient solution (⅛ M.S. salts). 200 mM NaCl was added to the watering solution at day 17 and at day 27 plants were watered with nutrient solution containing 250 mM NaCl. Plants were photographed 10 days after the last NaCl treatment. Identical conditions and treatment as described in Example 2 were used.

These transgenic plants are larger than wild-type plants. Furthermore, homozygous 35SAVP1 plants show sustained growth in the presence of 250 mM NaCl plus ⅛ M.S. salts when grown in a 24 hours light regimen. Interestingly, when 35SAVP1 plants were grown under short-day cycle conditions (12 hour day/light cycle) sustained growth in the presence of 300 mM NaCl plus ⅛ M.S. salts was observed.

Example 4

Hydroponically Grown Wild Type and 35SAVP1 Transgenic Plants

Hydroponically grown wild type and 35SAVP1 transgenic plants were generated. 65 days old wild type and 35SAVP1 transgenic plants grown in solution culture on a 12 hour light cycle.

Wild type and 35SAVP1 transgenic plants were also grown in solution culture on a 12 hours light cycle for 20 days. Starting at day 21, NaCl concentration was increased in a stepwise fashion by 50 mM increments every 4 days. Plants were photographed after 4 days in the presence of 200 mM NaCl.

Example 5

Double Transgenic Plant with 35S AVP1 and 35S AtNHX1

Overexpression of the pyrophosphate-energized vacuolar membrane proton pump AVP1 likely increases the availability of $H^+$ in the lumen of the vacuole, and the AtNHX1 $Na^+/H^+$ antiporter uses these $H^+$ to sequester $Na^+$ cations into the vacuole. Therefore, higher expression of these transporters likely maximizes the sequestration capability of the vacuole. To generate transgenic Arabidopsis plants that overexpress both genes AVP1 and AtNHX1, T3 35S AVP1 plants are used as females and T3 35S AtNHX1 plants are used as males. Female plants are hand-emasculated and anthers from freshly opened flowers of donor plants are harvested. With these anthers the emasculated plants are pollinated by touching the anthers onto the stigmas. The pollinated flowers are labeled and any remaining opened or unopened flowers from the same female plant are removed to avoid any confusion at harvest. The harvested seeds are sterilized using a 50% sodium hypochloride solution and mixed vigorously for 5 minutes and rinsed with water thoroughly. The sterilized seeds are stored in soft agar over night at 4° C. Then they are sprinkled onto solidified kanamycin-hygromycin selective medium. The 35S AVP1 construct has the neomycin phosphotransferase II gene that confers kanamycin tolerance in plants while the 35S AtNHX1 construct has a modified hygromycin B phosphotransferase that confers hygromycin tolerance in plants. The resistant seedlings are transplanted into soil and to the hydroponic media to be tested for their salt-tolerant phenotype. A transgenic Arabidopsis thaliana plant to overexpress the A. thaliana gain-of-function mutant gene AVP1-D (Zhen, et al., J. Biol. Chem., 272:22340-22348 (1997)) is engineered using the same double tandem enhancer of the 35A promoter described above (Topfer, R., et al., Nucl. Acid Res., 15:5890 (1997)). Plants overexpressing the gain of function mutant gene will likely show an enhanced phenotype. These plants are characterized in parallel with the 35SAVP1, 35S AtNHX singles and doubles trangenics. The A. thaliana gain-of-function mutant gene AVP1-D is subcloned into plasmid pRT103 carrying the 35S promoter and the polyadenylation signal of CaMV (Topfer, R., et al., Nucl. Acid Res., 15:5890 (1997)). A HindIII fragment containing the chimeric 35SAVP-D gene is subcloned into pBIBhyg (Becker, D., Nucl. Acid Res., 18:203 (1990)). The resulting T-DNA vector is transformed into Agrobacterium tumefaciens strain GV3101 via electroporation, and used for subsequent vacuum infiltration of Arabidopsis thaliana ecotype Columbia (Bechtold, N., et al., C. R. Jeances Acad. Sci. Ser. III Sci. Vie, 316:1194-1199 (1993)). Integration is confirmed on Southern blots of T3 plants and expression monitored on Northern blots of positive T3 plants.

Example 6

Comparative Transport Study with Vacuoles from the Roots of Wild-Type and 35S AVP1 Transgenic Plants The purpose of this study is to determine if the vacuoles of 35S AVP1 transgenic plants show a higher proton transport activity dependent on pyrophosphate. These determinations are done with root and shoot tissues separately from plants grown hydroponically. The transgene could show a tissue-specific regulation despite the 35S promoter.

In order to compare the PPi-dependent $H^+$ translocation activities of wild-type and 35S AVP1 transgenic plants sealed tonoplast-enriched vesicles from roots and leaves of the above plants are prepared. The homogenization and differential centrifugation procedure described by Rea and Turner (Rea, P. A., et al., Tonoplast Adenosine Triphosphate and Inorganic Pyrophosphatase. In: Meth. Plant Biochem., pp. 385-405, Academic Press limited, London (1990)) is followed. $H^+$ translocation is assayed fluorimetrically using acridine orange (2.5 µM) as transmembrane pH difference indicator in assay media containing vacuole membrane-enriched vesicles as described by Rea and coworkers (Zhen, R. G., et al., J. Biol. Chem., 272:22340-22348 (1997)). The assay media contains 300 µM Tris-PPi, 50 mK KCl, 2.5 µM acridine orange, 5 mM Tris-Mes (pH 8.0). Intravesicular acidification is triggered with the addition of 1.3 mM MgSO4 and terminated with the addition of the protonophore FCCP at 2.5 µM. Fluorescence is measured at excitation emission wavelengths of 495 and 540 nM, respectively, at a slit width of 5 nM (Zhen, R. G., et al., J. Biol. Chem., 269:23342-23350 (1994)). A further test to support that the $H^+$ translocation is AVP1 driven is the addition of the specific inhibitor aminomethylededi-phosphonate (Zhen, R. G., et al., Plant Physiol., 104:153-159 (1994)).

Example 7

Determination of the $Na^+/K^+$ Ratios in Leaves and Stems of the Transgenic Plants These measurements indicate to whether or not the transgenic plants described herein have an increased vacuolar capacity to sequester $Na^+$ in their leaves cells or elsewhere. Toxic concentrations of NaCl build up first in the fully expanded leaves where NaCl is compartmentalized in the vacuoles. Exposure to NaCl can disrupt or reduce $K^+$ uptake leading to $K^+$ deficiency and growth inhibition (Wu, S. J., et al., Plant Cell, 8:617-627 (1996). A cytosolic consequence of reduced $K^+$ content and high $Na^+$ is the inhibition of important enzymes. An example of such enzymes is the 3'(2'), 5'-bisphosphate nucleotidase of yeast whose activity is more sensitive to $Na^+$ when $K^+$ content is low (Murguia, JR., et al., Science, 267:232-234 (1995). To determine the $Na^+/K^+$ ratios in leaves and stemS wild-type and 35S AVP1/35S AtNHX1 double and single transgenics in hydroponic conditions (Gibeaut, D. M., et al., *Plant Physiol.*, 317-319 (1997) are grown. NaCl is added to the growth media in a stepwise fashion starting with 50 mM up to 250 mM (Apse, M., et al., *Science*, 285:1256-1258 (199). At every point the rosette and the stems of the treated plants are collected and their weight is determined. The samples are dried out in an oven at 80° C. and their dry weight is determined. The dry samples are boiled in a determined volume of water and their $Na^+$ and $K^+$ contents determined via atomic absorption spectrophotometry (Apse, M., et al., *Science*, 285:1256-1258 (1999); Gaxiola, R., et al., *Embo J.*, 11:3157-2164 (1992)).

Example 8

Determination of Whether 35S AVP1 Transgenic Plants are Larger Because their Cells are Larger or Because they have More Cells, or Both The shoot meristems labeling index is compared with one of the wild-type plants. Morphological and anatomical observations measuring and counting cells of leaves, roots and stems are performed. To determine if 35S AVP1 transgenic plants are larger because they have more cells, their shoot meristems labeling index is compared with the one of wild-type plants. To measure the DNA synthesis or cell proliferation 5-Bromo-2'-deoxy-uridine (BrdU) that can be incorporated into DNA in place of thymidine is used. Cells that have incorporated BrdU into DNA are detected using a monoclonal antibody against BrdU monoclonal antibody and an anti-mouse Ig-alkaline phosphatase as a second antibody. The bound anti-BrdU monoclonal antibody is visualized by light microscopy and the ratio between DAPI stained and BrdU positives established. The protocol is a modification of the one published by Chiatante and coworkers (Levi, M., et al., *Physiol. Plant.* 71:68-72 (1987)) and the BrdU labeling and detection kit II from Boehringer Mannheim. The plants are exposed for different times to the BrdU labeling medium and then fixation, paraffin embedding and sectioning is performed as described by Meyerowtz and coworkers (Drews, G., et al., *Plant Mol. Biol. Rep.*, 5:242-250 (1988)). For observation of leaf tissue, fresh tissues are embedded in 5% agarose and slice them with a microslicer. For primary root observation, seedlings are fixed for 4 hr in 50% ethanol, 5% acetic acid, and 3.7% formaldehyde at room temperature, dehydrate them in graded ethanol series, permeate them with xylene, and infiltrate them with paraffin. Eight-micrometer sections are stained with 0.05% toluidine blue and cells are counted under a microscope. As an alternative for the visualization and determination of cell size the method described by Greenberg and coworkers (Rate, et al., *The Plant Cell*, 11:1695-1708 (1999)) is followed.

Example 9

Isolation of Mutants in the Transporters

Genetic approaches are very powerful in analyzing complex biological traits (Serrano, R., *Crit. Rev. Plant Sci.*, 13:121-138 (1994)) Reverse genetics is a very important new tool for plant biologists. The generation of a good collection of tagged knockouts by Sussman and coworkers (Krysan, P., et al., *Proc. Natl. Acad. Sci. USA*, 93:8145-8150 (1996)) has opened a very important avenue for the analysis of gene disruptions in *Arabidopsis*. The Arabidopsis Knock-out Facility of the University of Wisconsin Madison is used to search among the 60,480 *Arabidopsis* (ecotype WS) lines that have been transformed with the T-DNA vector pD991 for the presence of T-DNA inserts within AtCLC-c, AtCLC-d, AVP1, AtNHX1 and their homologues. The phenotypes of the above knock-outs will shed light towards the understanding of the physiological roles of these transporters in normal and stress conditions. An initial characterization of the knockout plants includes testing for their salt tolerance and their $Na^+/K^+$ ratios. The generation of double knock-outs via crosses help to further understand the interaction among the transporters as well as the crosses with the 35S AVP1 and the 35S AtNHX1 transgenic plants.

To search for *Arabidopsis* knock-out PCR primers are designed following the guidelines detailed in the University of Wisconsin web site. Tested primers are sent to UW-Madison, where 62 PCR reactions that are sent to us for Southern blot analysis are performed. Positive PCR products are sequenced. If the sequence reveals that there is a T-DNA inserted within the gene the gene specific primers are sent for another set of PCR reactions in order to determine which of the 9 possible pools of 225 contains the knockout. After identifying the pool of interest, 25 tubes of seeds are screened for the individual plant carrying the T-DNA knock-out.

Example 10

Cation Detoxification in Plant Cells

The studies described herein together with other evidence strongly indicate that yeast and plants share pathways and signals for the trafficking of vesicles from Golgi network to the vacuole (Gaxiola, R., et al., *Proc. Natl. Acad. Sci. USA*, 96:1480-1485 (1999); Marty, F., "The Biogenesis of Vacuoles: Insights from Microscopy. In: *The Plant Vacuole*, 1-42, Leigh, R. A. and Sanders, D., Academic Press, San Diego (1997); Bassham, D. C., et al., *Plant Physiol*, 117:407-415 (1998)). Without wishing to be bound by theory, it is likely that in both systems a prevacuolar compartment is a dynamic entity that detoxifies the cytoplasm from toxic cations and delivers its cargo either to the vacuole, or directly to the cell exterior. Both the Gef1 chloride channel and Nhx1 $Na^+/H^+$ exchanger have been localized to the yeast prevacuolar compartment (Gaxiola, R. A., et al., *Proc. Natl. Acad. Sci. USA*, 96:1480-1485 (1999)). The behavior of the Gef1-GFP chimera in yeast cells in vivo have been monitored indicating that its localization varies depending the environmental conditions. Furthermore, it has been shown that two of the four *A. thaliana* CLC chloride channel genes CLC-c and -d are capable of suppressing gef1 mutant phenotypes implying a similar localization (Gaxiola, R. A., et al., *Proc. Natl. Acad. Sci. USA*, 95:4046-4050 (1998)). In order to understand how and where this cation detoxification takes place in plant cells the intracellular localization of GFP chimeras of AVP1, AtNHX1 and AtCLC-c and -d (Hong, B., et al., *Plant Physiol.*, 119:1165-1175 (1999)) is monitored in vivo. Confocal microscopy is also used to address colocalization of the different transporters. For this purpose HA-tagged versions or antibodies of the transporters under study are required (Guiltinan, M. J., et al., *Meth. Cell Biol.*, 49:143-151 (1995); Jauh, G.-Y., et al., *Plant Cell*, 11:1867-1882 (1999); Mullen, R. T., et al., *Plant. J.*, 12:313-322 (1997)).

For the construction of the GFP-chimeras the soluble versions of GFP with improved fluorescence in *A. thaliana* reported by Davis and Viestra (Davies, S. J., Viestra, R. D., "Soluble derivatives of green fluorescent protein (GFP) for use in *Arabidopsis thaliana*, (1998)) are used. Two types of GFP-chimeras are made, namely a set under the regulation of the native promoter and another set under the regulation of the 35S promoter. The resulting T-DNA vectors containing the GFP-chimeras are transformed into *Agrobacterium tumefaciens* strain GV3101 via electroporation, and used for subsequent vacuum infiltration of *Arabidopsis thaliana* ecotype Columbia (Bechtold, N., et al. *C. R. Jeances Acad. Sci. Ser. III Sci. Vie,* 316:1194-1199 (1993)). For the hemagglutinin (HA) epitope tagging a PCR strategy designed for yeast but modified to tag plant genes expressed in yeast vectors is used. Futcher and coworkers designed vectors containing the URA3 yeast gene flanked by direct repeats of epitope tags (HA) (Schneider, B. L., et al., *Yeast,* 11: 1265-1274 (1995)). Via PCR the tag-URA3-tag cassette is amplified such that the resulting PCR fragment possess homology at each end to the gene of interest. In vivo recombination in yeast is then used to direct the integration of the PCR-chimera to the plasmid carrying the plant ORF of interest, transformants are selected by the URA$^+$ phenotype. The URA3 gene is "popped out" when positive transformants are grown in the presence of 5-fluoro-orotic acid. The vector carrying the plant gene has a selection marker different than the URA3 gene.

Example 11

Further Applications of the Yeast Model

Gain of function mutants of the AtNHX that enhance salt tolerance of transgenic plants are generated using the yeast system. This is accomplished by mutagenizing the cloned gene to make a mutant library. This library is used to transform the salt sensitive yeast mutant ena1 and clones with an enhanced salt tolerant phenotype will be identified and retested. The other genes that show similarity to the AtNHX1 gene reported by the *Arabidopsis* Genome Initiative (AGI) are expressed in yeast. It is likely that some of these AtNHX1 homologues are plasma membrane transporters, so their function in yeast should be pH dependent. Thus the precise composition and pH of the medium used for screening is crucial for success. Identification of plasma membrane transporters helps to engineer plants with an enhanced salt tolerance due to a reduced sodium uptake. In addition, plant cDNA expression libraries in yeast are used to identify other families of transporters involved in NaCl detoxification.

To generate gain of function mutants of the AtNHX a method for introducing random mutations developed by Stratgene (Epicurian Coli XL1-Red competent Cells Cat#200129) is used. The method involves the propagation of a cloned gene into a strain deficient in the three primary DNA repair pathways. The random mutation rate in this strain is about 5000-fold higher than that of wild-type. A library of the mutated AtNHX gene is transformed into the ena1 yeast mutant and screened for salt tolerance. Yeast transformation is performed as described by Schiestl and coworkers (Gietz, D., et al., *Nucl. Acid Res.* 20:1425 (1992)). An alternative to the XL1-Red random mutagenesis strategy is a PCR approach described by Fink and coworkers (Madhani, H. D., et al., *Cell,* 91:673-684 (1997)). To test ATNHX1 homologues the same strains and conditions used for AtNHX1 (Gaxiola, R. A., et al., *Proc. Natl. Acad. Sci. USA,* 96:1480-1485 (1999)) are used initially. However, if these screening strains and/or conditions do not work new ones are worked out. It is likely that when dealing with plasma-membrane AtNHX1 homologues pH conditions of the assay media are crucial.

Example 12

Hydroponic Culture of Transgenic Plants

The reduced availability of fresh water for standard agriculture may force the use of alternative agricultural arts. It is conceivable that with salt tolerant crops the use of hydroponics with seawater will create a new era in crop production. As described herein, conditions for hydroponics culture of *Arabidopsis* plants have been established and their performance in increasing concentrations of NaCl in their media have been tested. Transgenic plants are challenged with a commercial seawater formula that contains the complete ionic composition present in the oceans.

35SAVP1, 35SAtNHX1 single and double transgenics are grown together with wildtype *Arabidopsis thaliana* plants under hydroponic conditions for four weeks in a short day illumination cycle (Gibeaut, D. M., et al., *Plant Physiol,* 317-319 (1997)). Then every four days an equivalent to 50 mM NaCl of Tropic Marin sea salt is added. This artificial sea water mix includes all of the other major and trace elements present in real sea water. Growth is monitored and physiological parameters, such as sodium content and distribution is determined as described in previous sections.

The effects of the overexpression of these *Arabidopsis thaliana* proton transporters (AVP1 and AtNHX1) in more agriculturally important plants such as tomato are examined. The tomato homologues of AVP1 and AtNHX1 are isolated and the corresponding chimeras to overexpress them are constructed (Bidone, S., et al., *Eur. J. Biochem.,* 253: 20-26 (1998); Burbidge, A., et al, *J. Exper. Botany,* 48:2111-2112 (1997)). The genes are introduced via *Agrobacterium*-mediated infection of calli. Tissue culture methods are used to regenerate transformed plants. The plants are assayed for salt tolerance as well as physiological parameters, such as sodium content and distribution. Increasing the salt-tolerance of tomato plants will likely have important economic repercussions. A positive result indicates that the sequestration model described herein is also applicable to an important crop. Tomato transformation with 35S AVP1 and with 35S AtNHX1 constructs is performed as described by McCormick (McCormick, S., Transformation of tomato with *Agrobacterium tumefaciens*. In: *Plant Tissue Culture Manual,* pp. 1-9, Lindsey, K. (ed.), Kluwer Academic Publishers, Dordrecht, The Netherlands (1991)). T0 and T1 transgenics are analyzed by polymerase chain reaction and DNA gel blotting for the presence and copy number of AVP1 and AtNHX1 transgenes. Heterozygous and homozygous plants are identified after segregation analysis of each transcend within T1 seeds. Homozygous plants are assayed for salt tolerance and as well as physiological parameters, such as sodium content and distribution. Degenerated oligos based on conserved sequences present in AVP1 and AtNHX1 homologues are designed. These degenerated primers are used in RT-PCR reactions with cDNAs made from poly(A)+RNA from tomato. The resulting PCR fragments are used as probes to isolate the full length cDNA clones from commercial libraries (i.e. Stratagene Cat#936004). A similar strategy was described by Caboche and coworkers (Quesada, A., et al., *Plant Mol. Biol.,* 34:265-274 (1997)).

While this invention has been particularly shown and described with references to preferred embodiments thereof, it will be understood by those skilled in the art that various changes in form and details may be made therein without departing from the scope of the invention encompassed by the appended claims.

What is claimed is:

1. One or more transgenic plant cells, comprising an exogenous nucleic acid that causes overexpression of a plant vacuolar pyrophosphatase in the one or more transgenic plant cells, wherein the exogenous nucleic acid comprises a nucleic acid encoding the plant vacuolar pyrophosphatase, and the plant vacuolar pyrophosphatase is AVP1 or a homolog thereof, and wherein said homolog has plant vacuolar pyrophosphatase activity.

2. The one or more transgenic plant cells of claim 1, wherein the transgenic plant cells are cells from a plant selected from the group consisting of tomato, rice, tobacco, sorghum, cucumber, lettuce, turf grass, *Arabidopsis* and corn.

3. The one or more transgenic plant cells of claim 1, wherein the transgenic plant cells are obtained from a tissue selected from the group consisting of roots, stems, leaves, flowers, fruits and seeds.

4. The one or more transgenic plant cells of claim 1, wherein the nucleic acid encoding the plant vacuolar pyrophosphatase is from a non-transgenic wild-type plant of the same species as the transgenic plant.

5. The one or more transgenic plant cells of claim 1, wherein the nucleic acid encoding the plant vacuolar pyrophosphatase is from a non-transgenic wild-type plant of a species different from the transgenic plant.

6. The one or more transgenic plant cells of claim 1, wherein the nucleic acid encoding the plant vacuolar pyrophosphatase is obtained from a plant selected from the group consisting of *Arabidopsis*, tobacco, tomato and corn.

7. The one or more transgenic plant cells of claim 1, wherein the nucleic acid encoding the plant vacuolar pyrophosphatase is operably linked to at least one regulatory element that results in overexpression of the plant vacuolar pyrophosphatase.

8. The one or more transgenic plant cells of claim 7, wherein the regulatory element is selected from the group consisting of tissue-specific promoters, constitutive promoters, inducible promoters and promoters that are both tissue-specific and inducible.

9. The one or more transgenic plant cells of claim 8, wherein the nucleic acid encoding the plant vacuolar pyrophosphatase is operably linked to a double tandem enhancer of a 35S CaMV promoter.

10. A transgenic plant, comprising transgenic plant cells comprising an exogenous nucleic acid that causes overexpression of a plant vacuolar pyrophosphatase in the transgenic plant cells, wherein the exogenous nucleic acid comprises a nucleic acid encoding the plant vacuolar pyrophosphatase, and the plant vacuolar pyrophosphatase is AVP1 or a homolog thereof, and wherein said homolog has plant vacuolar pyrophosphatase activity.

11. The transgenic plant of claim 10, wherein the transgenic plant is selected from the group consisting of tomato, rice, tobacco, sorghum, cucumber, lettuce, turf grass, *Arabidopsis* and corn.

12. The transgenic plant of claim 10, wherein the nucleic acid encoding the plant vacuolar pyrophosphatase is from a non-transgenic wild-type plant of the same species as the transgenic plant.

13. The transgenic plant of claim 10, wherein the nucleic acid encoding the plant vacuolar pyrophosphatase is from a non-transgenic wild-type plant of a species different from the transgenic plant.

14. The transgenic plant of claim 10, wherein the nucleic acid encoding the plant vacuolar pyrophosphatase is obtained from a plant selected from the group consisting of *Arabidopsis*, tobacco, tomato and corn.

15. The transgenic plant of claim 10, wherein the nucleic acid encoding the plant vacuolar pyrophosphatase is operably linked to at least one regulatory element that results in overexpression of the plant vacuolar pyrophosphatase.

16. The transgenic plant of claim 15, wherein the regulatory element is selected from the group consisting of tissue-specific promoters, constitutive promoters, inducible promoters and promoters that are both tissue-specific and inducible.

17. The transgenic plant of claim 16, wherein the nucleic acid encoding the plant vacuolar pyrophosphatase is operably linked to a double tandem enhancer of a 35S CaMV promoter.

18. Transgenic progeny of the transgenic plant of claim 10, wherein the transgenic progeny comprises the exogenous nucleic acid of claim 10.

19. Transgenic seeds produced by the transgenic plant of claim 10, wherein the transgenic seeds comprise the exogenous nucleic acid of claim 10.

20. Transgenic progeny grown from the transgenic seeds of claim 19.

21. The transgenic plant of claim 10, wherein the transgenic plant has one or more enhanced phenotypic traits relative to non-transgenic wild-type plants of the same species, and the enhanced phenotypic traits are selected from the group consisting of increased tolerance to one or more salts, increased yield and larger plant size.

22. The transgenic plant of claim 21, wherein the one or more salts are selected from the group consisting of NaCl, KCl and $CaCl_2$.

23. The transgenic plant of claim 21, wherein the one or more salts have a concentration of about 0.2M to about 0.3M in water.

24. A method of making a transgenic plant with one or more enhanced phenotypic traits relative to non-transgenic wild-type plants of the same species, wherein the enhanced phenotypic traits are selected from the group consisting of increased tolerance to one or more salts, increased yield and larger plant size, said method comprising:
 a) introducing an exogenous nucleic acid comprising a nucleic acid encoding a plant vacuolar pyrophosphatase into one or more cells of a plant to produce transformed cells, wherein the plant vacuolar pyrophosphatase is AVP1 or a homolog thereof, and wherein said homolog has plant vacuolar pyrophosphatase activity;
 b) regenerating transgenic plants from the transformed cells; and
 c) selecting a transgenic plant with one or more enhanced phenotypic traits relative to non-transgenic wild-type plants of the same species, wherein the enhanced phenotypic traits are selected from the group consisting of increased tolerance to one or more salts, increased yield and larger plant size, thereby producing the transgenic plant.

25. The method of claim 24, wherein the transgenic plant is selected from the group consisting of tomato, rice, tobacco, sorghum, cucumber, lettuce, turf grass, *Arabidopsis* and corn.

26. The method of claim 24, wherein the one or more cells of a plant are obtained from a tissue selected from the group consisting of roots, stems, leaves, flowers, fruits and seeds.

27. The method of claim 24, wherein the nucleic acid encoding a plant vacuolar pyrophosphatase is from a non-transgenic wild-type plant of the same species as the transgenic plant.

28. The method of claim 24, wherein the nucleic acid encoding a plant vacuolar pyrophosphatase is from a non-transgenic wild-type plant of a species different from the transgenic plant.

29. The method of claim 24, wherein the nucleic acid encoding a plant vacuolar pyrophosphatase is obtained from a plant selected from the group consisting of *Arabidopsis*, tobacco, tomato and corn.

30. The method of claim 24, wherein the nucleic acid encoding a plant vacuolar pyrophosphatase is operably linked to at least one regulatory element that results in overexpression of the plant vacuolar pyrophosphatase.

31. The method of claim 30, wherein the regulatory element is selected from the group consisting of tissue-specific promoters, constitutive promoters, inducible promoters and promoters that are both tissue-specific and inducible.

32. The method of claim 31, wherein the nucleic acid encoding a plant vacuolar pyrophosphatase is operably linked to a double tandem enhancer of a 35S CaMV promoter.

33. The method of claim 24, wherein the one or more salts are selected from the group consisting of NaCl, KCl and $CaCl_2$.

34. The method of claim 24, wherein the one or more salts have a concentration of about 0.2M to about 0.3M in water.

* * * * *

SEQUENCE LISTING

<160> NUMBER OF SEQ ID NOS: 7

<210> SEQ ID NO 1
<211> LENGTH: 538
<212> TYPE: PRT
<213> ORGANISM: Artificial Sequence
<220> FEATURE:
<223> OTHER INFORMATION: Arabidpsis - AtNhx1

<400> SEQUENCE: 1

```
Met Leu Asp Ser Leu Val Ser Lys Leu Pro Ser Leu Ser Thr Ser Asp
 1               5                  10                  15
His Ala Ser Val Val Ala Leu Asn Leu Phe Val Ala Leu Leu Cys Ala
             20                  25                  30
Cys Ile Val Leu Gly His Leu Leu Glu Glu Asn Arg Trp Met Asn Glu
         35                  40                  45
Ser Ile Thr Ala Leu Leu Ile Gly Leu Gly Thr Gly Val Thr Ile Leu
     50                  55                  60
Leu Ile Ser Lys Gly Lys Ser Ser His Leu Leu Val Phe Ser Glu Asp
65                  70                  75                  80
Leu Phe Phe Ile Tyr Leu Leu Pro Pro Ile Ile Phe Asn Ala Gly Phe
                 85                  90                  95
Gln Val Lys Lys Lys Gln Phe Phe Arg Asn Phe Val Thr Ile Met Leu
            100                 105                 110
Phe Gly Ala Val Gly Thr Ile Ile Ser Cys Thr Ile Ile Ser Leu Gly
        115                 120                 125
Val Thr Gln Phe Phe Lys Lys Leu Asp Ile Gly Thr Phe Asp Leu Gly
    130                 135                 140
Asp Tyr Leu Ala Ile Gly Ala Ile Phe Ala Ala Thr Asp Ser Val Cys
145                 150                 155                 160
Thr Leu Gln Val Leu Asn Gln Asp Glu Thr Pro Leu Leu Tyr Ser Leu
                165                 170                 175
Val Phe Gly Glu Gly Val Val Asn Asp Ala Thr Ser Val Val Val Phe
            180                 185                 190
Asn Ala Ile Gln Ser Phe Asp Leu Thr His Leu Asn His Glu Ala Ala
        195                 200                 205
Phe His Leu Leu Gly Asn Phe Leu Tyr Leu Phe Leu Leu Ser Thr Leu
    210                 215                 220
Leu Gly Ala Ala Thr Gly Leu Ile Ser Ala Tyr Val Ile Lys Lys Leu
225                 230                 235                 240
Tyr Phe Gly Arg His Ser Thr Asp Arg Glu Val Ala Leu Met Met Leu
                245                 250                 255
Met Ala Tyr Leu Ser Tyr Met Leu Ala Glu Leu Phe Asp Leu Ser Gly
            260                 265                 270
Ile Leu Thr Val Phe Phe Cys Gly Ile Val Met Ser His Tyr Thr Trp
        275                 280                 285
His Asn Val Thr Glu Ser Ser Arg Ile Thr Thr Lys His Thr Phe Ala
    290                 295                 300
Thr Leu Ser Phe Leu Ala Glu Thr Phe Ile Phe Leu Tyr Val Gly Met
305                 310                 315                 320
Asp Ala Leu Asp Ile Asp Lys Trp Arg Ser Val Ser Asp Thr Pro Gly
                325                 330                 335
Thr Ser Ile Ala Val Ser Ser Ile Leu Met Gly Leu Val Met Val Gly
            340                 345                 350
```

```
Arg Ala Ala Phe Val Phe Pro Leu Ser Phe Ser Asn Leu Ala Lys
        355                 360                 365
Lys Asn Gln Ser Glu Lys Ile Asn Phe Asn Met Gln Val Val Ile Trp
    370                 375                 380
Trp Ser Gly Leu Met Arg Gly Ala Val Ser Met Ala Leu Ala Tyr Asn
385                 390                 395                 400
Lys Phe Thr Arg Ala Gly His Thr Asp Val Arg Gly Asn Ala Ile Met
                405                 410                 415
Ile Thr Ser Thr Ile Thr Val Cys Leu Phe Ser Thr Val Val Phe Gly
                420                 425                 430
Met Leu Thr Lys Pro Leu Ile Ser Tyr Leu Leu Pro His Gln Asn Ala
            435                 440                 445
Thr Thr Ser Met Leu Ser Asp Asp Asn Thr Pro Lys Ser Ile His Ile
        450                 455                 460
Pro Leu Leu Asp Gln Asp Ser Phe Ile Glu Pro Ser Gly Asn His Asn
465                 470                 475                 480
Val Pro Arg Pro Asp Ser Ile Arg Gly Phe Leu Thr Arg Pro Thr Arg
                485                 490                 495
Thr Val His Tyr Tyr Trp Arg Gln Phe Asp Asp Ser Phe Met Arg Pro
                500                 505                 510
Val Phe Gly Gly Arg Gly Phe Val Pro Phe Val Pro Gly Ser Pro Thr
            515                 520                 525
Glu Arg Asn Pro Pro Asp Leu Ser Lys Ala
        530                 535

<210> SEQ ID NO 2
<211> LENGTH: 669
<212> TYPE: PRT
<213> ORGANISM: Artificial Sequence
<220> FEATURE:
<223> OTHER INFORMATION: Human - HsNhe-6

<400> SEQUENCE: 2

Met Ala Arg Arg Gly Trp Arg Arg Ala Pro Leu Arg Gly Val Gly
  1               5                  10                  15
Ser Ser Pro Arg Ala Arg Arg Leu Met Arg Pro Leu Trp Leu Leu Leu
                 20                  25                  30
Ala Val Gly Val Phe Asp Trp Ala Gly Ala Ser Asp Gly Gly Gly Gly
             35                  40                  45
Glu Ala Arg Ala Met Asp Glu Glu Ile Val Ser Glu Lys Gln Ala Glu
         50                  55                  60
Glu Ser His Arg Gln Asp Ser Ala Asn Leu Leu Ile Phe Ile Leu Leu
 65                  70                  75                  80
Leu Thr Leu Thr Ile Leu Thr Ile Trp Leu Phe Lys His Arg Arg Ala
                 85                  90                  95
Arg Phe Leu His Glu Thr Gly Leu Ala Met Ile Tyr Gly Leu Leu Val
                100                 105                 110
Gly Leu Val Leu His Tyr Gly Ile His Val Pro Ser Asp Val Asn Asn
            115                 120                 125
Val Thr Leu Ser Cys Glu Val Gln Ser Ser Pro Thr Thr Leu Leu Val
        130                 135                 140
Thr Phe Asp Pro Glu Val Phe Asn Ile Leu Leu Pro Pro Ile Ile
145                 150                 155                 160
Phe Tyr Ala Gly Tyr Ser Leu Lys Arg Arg His Phe Phe Arg Asn Leu
                165                 170                 175
Gly Ser Ile Leu Ala Tyr Ala Phe Leu Gly Thr Ala Ile Ser Cys Phe
```

-continued

```
                  180                 185                 190
Val Ile Gly Ser Ile Met Tyr Gly Val Thr Leu Met Lys Val Thr
              195                 200                 205
Gly Gln Leu Ala Gly Asp Phe Tyr Phe Thr Asp Cys Leu Leu Phe Gly
          210                 215                 220
Ala Ile Val Ser Ala Thr Asp Pro Val Thr Leu Ala Ile Phe His
225                 230                 235                 240
Glu Leu Gln Val Asp Val Glu Leu Tyr Ala Leu Leu Phe Gly Glu Ser
                  245                 250                 255
Val Leu Asn Asp Ala Val Ala Ile Val Leu Ser Ser Ser Ile Val Ala
              260                 265                 270
Tyr Gln Pro Ala Gly Asp Asn Ser His Thr Phe Asp Val Thr Ala Met
              275                 280                 285
Phe Lys Ser Ile Gly Ile Phe Leu Gly Ile Phe Ser Gly Ser Phe Ala
              290                 295                 300
Met Gly Ala Ala Thr Gly Val Val Thr Ala Leu Val Thr Lys Phe Thr
305                 310                 315                 320
Lys Leu Arg Glu Phe Gln Leu Leu Glu Thr Gly Leu Phe Phe Leu Met
                  325                 330                 335
Ser Trp Ser Thr Phe Leu Leu Ala Glu Ala Trp Gly Phe Thr Gly Val
              340                 345                 350
Val Ala Val Leu Phe Cys Gly Ile Thr Gln Ala His Tyr Thr Tyr Asn
              355                 360                 365
Asn Leu Ser Thr Glu Ser Gln His Arg Thr Lys Gln Leu Phe Glu Leu
          370                 375                 380
Leu Asn Phe Leu Ala Glu Asn Phe Ile Phe Ser Tyr Met Gly Leu Thr
385                 390                 395                 400
Leu Phe Thr Phe Gln Asn His Val Phe Asn Pro Thr Phe Val Val Gly
                  405                 410                 415
Ala Phe Val Ala Ile Phe Leu Gly Arg Ala Ala Asn Ile Tyr Pro Leu
              420                 425                 430
Ser Leu Leu Leu Asn Leu Gly Arg Arg Ser Lys Ile Gly Ser Asn Phe
          435                 440                 445
Gln His Met Met Met Phe Ala Gly Leu Arg Gly Ala Met Ala Phe Ala
          450                 455                 460
Leu Ala Ile Arg Asp Thr Ala Thr Tyr Ala Arg Gln Met Met Phe Ser
465                 470                 475                 480
Thr Thr Leu Leu Ile Val Phe Phe Thr Val Trp Val Phe Gly Gly Gly
                  485                 490                 495
Thr Thr Ala Met Leu Ser Cys Leu His Ile Arg Val Gly Val Asp Ser
              500                 505                 510
Asp Gln Glu His Leu Gly Val Pro Glu Asn Glu Arg Arg Thr Thr Lys
          515                 520                 525
Ala Glu Ser Ala Trp Leu Phe Arg Met Trp Tyr Asn Phe Asp His Asn
          530                 535                 540
Tyr Leu Lys Pro Leu Leu Thr His Ser Gly Pro Pro Leu Thr Thr Thr
545                 550                 555                 560
Leu Pro Ala Cys Cys Gly Pro Ile Ala Arg Cys Leu Thr Ser Pro Gln
                  565                 570                 575
Ala Tyr Glu Asn Gln Glu Gln Leu Lys Asp Asp Ser Asp Leu Ile
              580                 585                 590
Leu Asn Asp Gly Asp Ile Ser Leu Thr Tyr Gly Asp Ser Thr Val Asn
              595                 600                 605
```

```
Thr Glu Pro Ala Thr Ser Ser Ala Pro Arg Arg Phe Met Gly Asn Ser
        610                 615                 620

Ser Glu Asp Ala Leu Asp Arg Glu Leu Ala Phe Gly Asp His Glu Leu
625                 630                 635                 640

Val Ile Arg Gly Thr Arg Leu Val Leu Pro Met Asp Asp Ser Glu Pro
                645                 650                 655

Pro Leu Asn Leu Leu Asp Asn Thr Arg His Gly Pro Ala
        660                 665

<210> SEQ ID NO 3
<211> LENGTH: 633
<212> TYPE: PRT
<213> ORGANISM: Artificial Sequence
<220> FEATURE:
<223> OTHER INFORMATION: Yeast - ScNhx1

<400> SEQUENCE: 3

Met Leu Ser Lys Val Leu Leu Asn Ile Ala Phe Lys Val Leu Leu Thr
1               5                   10                  15

Thr Ala Lys Arg Ala Val Asp Pro Asp Asp Asp Glu Leu Leu Pro
            20                  25                  30

Ser Pro Asp Leu Pro Gly Ser Asp Pro Ile Ala Gly Asp Pro Asp
        35                  40                  45

Val Asp Leu Asn Pro Val Thr Glu Glu Met Phe Ser Ser Trp Ala Leu
50                  55                  60

Phe Ile Met Leu Leu Leu Ile Ser Ala Leu Trp Ser Ser Tyr Tyr
65                  70                  75                  80

Leu Thr Gln Lys Arg Ile Arg Ala Val His Glu Thr Val Leu Ser Ile
                85                  90                  95

Phe Tyr Gly Met Val Ile Gly Leu Ile Ile Arg Met Ser Pro Gly His
                100                 105                 110

Tyr Ile Gln Asp Thr Val Thr Phe Asn Ser Ser Tyr Phe Phe Asn Val
            115                 120                 125

Leu Leu Pro Pro Ile Ile Leu Asn Ser Gly Tyr Glu Leu Asn Gln Val
130                 135                 140

Asn Phe Phe Asn Asn Met Leu Ser Ile Leu Ile Phe Ala Ile Pro Gly
145                 150                 155                 160

Thr Phe Ile Ser Ala Val Val Ile Gly Ile Ile Leu Tyr Ile Trp Thr
                165                 170                 175

Phe Leu Gly Leu Glu Ser Ile Asp Ile Ser Phe Ala Asp Ala Met Ser
            180                 185                 190

Val Gly Ala Thr Leu Ser Ala Thr Asp Pro Val Thr Ile Leu Ser Ile
        195                 200                 205

Phe Asn Ala Tyr Lys Val Asp Pro Lys Leu Tyr Thr Ile Ile Phe Gly
210                 215                 220

Glu Ser Leu Leu Asn Asp Ala Ile Ser Ile Val Met Phe Glu Thr Cys
225                 230                 235                 240

Gln Lys Phe His Gly Gln Pro Ala Thr Phe Ser Ser Val Phe Glu Gly
                245                 250                 255

Ala Gly Leu Phe Leu Met Thr Phe Ser Val Ser Leu Leu Ile Gly Val
            260                 265                 270

Leu Ile Gly Ile Leu Val Ala Leu Leu Lys His Thr His Ile Arg
        275                 280                 285

Arg Tyr Pro Gln Ile Glu Ser Cys Leu Ile Leu Leu Ile Ala Tyr Glu
290                 295                 300

Ser Tyr Phe Phe Ser Asn Gly Cys His Met Ser Gly Ile Val Ser Leu
```

```
              305                 310                 315                 320
Leu Phe Cys Gly Ile Thr Leu Lys His Tyr Ala Tyr Tyr Asn Met Ser
                325                 330                 335

Arg Arg Ser Gln Ile Thr Ile Lys Tyr Ile Phe Gln Leu Leu Ala Arg
            340                 345                 350

Leu Ser Glu Asn Phe Ile Phe Ile Tyr Leu Gly Leu Glu Leu Phe Thr
        355                 360                 365

Glu Val Glu Leu Val Tyr Lys Pro Leu Leu Ile Ile Val Ala Ala Ile
    370                 375                 380

Ser Ile Cys Val Ala Arg Trp Cys Ala Val Phe Pro Leu Ser Gln Phe
385                 390                 395                 400

Val Asn Trp Ile Tyr Arg Val Lys Thr Ile Arg Ser Met Ser Gly Ile
                405                 410                 415

Thr Gly Glu Asn Ile Ser Val Pro Asp Glu Ile Pro Tyr Asn Tyr Gln
            420                 425                 430

Met Met Thr Phe Trp Ala Gly Leu Arg Gly Ala Val Gly Val Ala Leu
        435                 440                 445

Ala Leu Gly Ile Gln Gly Glu Tyr Lys Phe Thr Leu Leu Ala Thr Val
    450                 455                 460

Leu Val Val Val Leu Thr Val Ile Ile Phe Gly Thr Thr Ala
465                 470                 475                 480

Gly Met Leu Glu Val Leu Asn Ile Lys Thr Gly Cys Ile Ser Glu Glu
                485                 490                 495

Asp Thr Ser Asp Asp Glu Phe Asp Ile Glu Ala Pro Arg Ala Ile Asn
            500                 505                 510

Leu Leu Asn Gly Ser Ser Ile Gln Thr Asp Leu Gly Pro Tyr Ser Asp
        515                 520                 525

Asn Asn Ser Pro Asp Ile Ser Ile Asp Gln Phe Ala Val Ser Ser Asn
    530                 535                 540

Lys Asn Leu Pro Asn Asn Ile Ser Thr Thr Gly Gly Asn Thr Phe Gly
545                 550                 555                 560

Gly Leu Asn Glu Thr Glu Asn Thr Ser Pro Asn Pro Ala Arg Ser Ser
                565                 570                 575

Met Asp Lys Arg Asn Leu Arg Asp Lys Leu Gly Thr Ile Phe Asn Ser
            580                 585                 590

Asp Ser Gln Trp Phe Gln Asn Phe Asp Glu Gln Val Leu Lys Pro Val
        595                 600                 605

Phe Leu Asp Asn Val Ser Pro Ser Leu Gln Asp Ser Ala Thr Gln Ser
    610                 615                 620

Pro Ala Asp Phe Ser Ser Gln Asn His
625                 630

<210> SEQ ID NO 4
<211> LENGTH: 11
<212> TYPE: PRT
<213> ORGANISM: Unknown
<220> FEATURE:
<223> OTHER INFORMATION: Putative Amiloride Binding Site From Human Nhe1

<400> SEQUENCE: 4

Asp Val Phe Phe Leu Phe Leu Leu Pro Pro Ile
 1               5                  10

<210> SEQ ID NO 5
<211> LENGTH: 38
<212> TYPE: DNA
<213> ORGANISM: Artificial Sequence
```

<220> FEATURE:
<223> OTHER INFORMATION: PCR primer used to amplify AtNHX1 ORF

<400> SEQUENCE: 5
ggcccgggat ggattctcta gtgtcgaaac tgccttcg                                    38

<210> SEQ ID NO 6
<211> LENGTH: 2813
<212> TYPE: DNA
<213> ORGANISM: Arabidopsis thaliana

<400> SEQUENCE: 6
cttagattta tctttgagtc ccgaaacatc gaggaacgcc ttcgaatccc tctctctctg      60
tgtgtgttct ctgtgttctc tctctcgcgc gaagcggttc tctttctttt gtttatttgt     120
ttttatttgt ttttctctta tacggaggag agaagatggt ggcgcctgct tgttaccgg      180 agctctggac ggagatcctt gtaccgattt gtgcggtgat tggtatcgcc ttttcgcttt     240
tccaatggta cgttgtatct cgcgtgaaac tcacctctga cctcggcgca tcgtcttccg     300
gtggagctaa caatgggaag aatggatacg tgattatct aatcgaggaa gaggaaggtg      360
ttaatgacca gagtgttgtc gctaagtgcg ctgagattca gactgctatt ccgaaggtg      420 caacttcatt cctattcacg gagtacaaat atgttggtgt cttcatgatt ttctttgctg     480
ctgttatctt tgtttttcctc ggctctgttg agggattcag cactgataac aagccttgta    540
cttacgacac caccagaacc tgcaagcctg cattggctac tgcagctttc agtaccattg     600 cttttcgtgct tggtgctgtt acctctgttc tatctggttt ccttgggatg aagattgcta    660
catacgctaa tgctaggacc actttggagg cgaggaaagg tgttggaaag gcgttcattg     720
ttgcattcag gtctggtgct gtgatgggtt tccttcttgc agcgagtggt ctattggtgc     780
tttacattac tatcaatgtg ttcaagatct attacggaga tgactgggaa ggtctttttg     840
aggctattac tggttatggt cttggtgggt cttccatggc tctctttggc cgtgttggtg     900
gtgggatcta cactaaggct gctgatgtcg gcgctgaccct tgtcggtaaa attgagagga    960
atattccaga ggatgatcca agaaacccag ctgtcattgc tgataatgtc ggtgacaatg    1020
ttggtgacat tgctggtatg ggatctgatc tcttttggatc atatgctgaa gcatcatgcg    1080
ctgctcttgt tgttgcctcg atctcatctt tcggaatcaa ccacgacttc actgccatgt    1140
gctacccatt gctcatcagt tcaatgggaa tcttggtttg tttgatcaca actctctttg    1200
ccactgactt ctttgagatt aagcttgtca aggagattga accagcattg aagaaccagc    1260
tcattatctc aactgttatt atgactgttg gtattgctat tgtgtcatgg gttggcttac    1320
cgacctcctt taccatcttc aactttggaa cacaaaaagt tgtcaagaac tggcagctat    1380
tcctttgtgt ttgtgttggt ctttgggctg gactcattat tggtttcgtc actgagtact    1440
acactagtaa cgcctacagc cctgtgcaag atgttgcaga ttcatgcaga actggtgcag    1500
ctaccaatgt tatcttcggc cttgctcttg gttacaaatc cgtcattatt ccaatctttg    1560
ctattgctat cagtatattc gttagcttca gctttgctgc tatgtatggt gttgctgttg    1620
ctgctcttgg tatgctcagt accattgcca ctggtttggc aattgatgct tatggtccca    1680
tcagtgacaa tgctggtggt attgctgaaa tggctggaat gagccaccgc atccgtgaaa    1740
gaactgatgc tcttgatgcc gctggaaaca ccactgctgc tattggaaag ggatttgcca    1800
ttggctctgc tgccctagtc tccttggctc tcttggtgc ctttgtgagc cgtgcaggga    1860
tccacaccgt agatgttttg accctaaag ttatcattgg ctccttgtt ggtgccatgc     1920 ttccttactg gttctctgcc atgacaatga agagtgtggg aagtgcagct cttaagatgg    1980

```
ttgaagaagt cgcaggcag ttcaacacca tccctggact tatggaagga accgcaaaac   2040
cagactacgc cacatgtgtc aagatctcca ccgatgcttc catcaaggaa atgatacctc   2100
ctggttgcct tgtcatgctc acacctctca ttgttggttt cttctttgga gttgagaccc   2160
tctctggtgt cctcgccgga tctcttgtat ccggtgttca gatcgccata tcagcatcta   2220
acactggtgg tgcctgggac aacgccaaga aatacatcga ggctggtgta tcagagcacg   2280
caaagagcct tggaccaaag ggttcagagc acacaaggc agctgtgatt ggagacacaa    2340
ttggagaccc attgaaggat acttcaggac cttcattgaa catcctcatc aagctcatgg   2400
ctgttgagtc tcttgtcttt gctcccttct tcgccactca cggtggtatc cttttcaagt   2460
acttctaaac tcaatccgag ggaagaagat gacgatgatg aagaagaaga agatgatgat   2520
ggcgatcgat tctaaacttt cttttttacc attcttattt tcgtttaccg taggtggtta   2580 aaaaacctt ttgttgatga ggctcattta aagaaccaac caaatgatgt ttctttctct    2640
cactctctgt ctttctgttt tcttttttgtt ctgtttagaa tttagaaatc caccaagtat   2700
tcggtcgaga cttgttttag ccgttacttt ctgctgctta tatttcctaa attggttgtc   2760
ttcttcgaaa cataattgga atttattgtt actgttagtc taaaaaaaaa aaa           2813
```

<210> SEQ ID NO 7
<211> LENGTH: 770
<212> TYPE: PRT
<213> ORGANISM: Arabidopsis thaliana

<400> SEQUENCE: 7

```
Met Val Ala Pro Ala Leu Leu Pro Glu Leu Trp Thr Glu Ile Leu Val
 1               5                  10                  15

Pro Ile Cys Ala Val Ile Gly Ile Ala Phe Ser Leu Phe Gln Trp Tyr
            20                  25                  30

Val Val Ser Arg Val Lys Leu Thr Ser Asp Leu Gly Ala Ser Ser Ser
        35                  40                  45

Gly Gly Ala Asn Asn Gly Lys Asn Gly Tyr Gly Asp Tyr Leu Ile Glu
    50                  55                  60

Glu Glu Glu Gly Val Asn Asp Gln Ser Val Val Ala Lys Cys Ala Glu
65                  70                  75                  80

Ile Gln Thr Ala Ile Ser Glu Gly Ala Thr Ser Phe Leu Phe Thr Glu
                85                  90                  95

Tyr Lys Tyr Val Gly Val Phe Met Ile Phe Phe Ala Ala Val Ile Phe
            100                 105                 110

Val Phe Leu Gly Ser Val Glu Gly Phe Ser Thr Asp Asn Lys Pro Cys
        115                 120                 125

Thr Tyr Asp Thr Thr Arg Thr Cys Lys Pro Ala Leu Ala Thr Ala Ala
    130                 135                 140

Phe Ser Thr Ile Ala Phe Val Leu Gly Ala Val Thr Ser Val Leu Ser
145                 150                 155                 160

Gly Phe Leu Gly Met Lys Ile Ala Thr Tyr Ala Asn Ala Arg Thr Thr
                165                 170                 175

Leu Glu Ala Arg Lys Gly Val Gly Lys Ala Phe Ile Val Ala Phe Arg
            180                 185                 190

Ser Gly Ala Val Met Gly Phe Leu Leu Ala Ala Ser Gly Leu Leu Val
        195                 200                 205

Leu Tyr Ile Thr Ile Asn Val Phe Lys Ile Tyr Tyr Gly Asp Asp Trp
    210                 215                 220

Glu Gly Leu Phe Glu Ala Ile Thr Gly Tyr Gly Leu Gly Gly Ser Ser
```

```
            225                 230                 235                 240
        Met Ala Leu Phe Gly Arg Val Gly Gly Ile Tyr Thr Lys Ala Ala
                        245                 250                 255

Asp Val Gly Ala Asp Leu Val Gly Lys Ile Glu Arg Asn Ile Pro Glu
                    260                 265                 270

Asp Asp Pro Arg Asn Pro Ala Val Ile Ala Asp Asn Val Gly Asp Asn
                    275                 280                 285

Val Gly Asp Ile Ala Gly Met Gly Ser Asp Leu Phe Gly Ser Tyr Ala
                    290                 295                 300

Glu Ala Ser Cys Ala Ala Leu Val Val Ala Ser Ile Ser Ser Phe Gly
        305                 310                 315                 320

Ile Asn His Asp Phe Thr Ala Met Cys Tyr Pro Leu Leu Ile Ser Ser
                        325                 330                 335

Met Gly Ile Leu Val Cys Leu Ile Thr Thr Leu Phe Ala Thr Asp Phe
                        340                 345                 350

Phe Glu Ile Lys Leu Val Lys Glu Ile Glu Pro Ala Leu Lys Asn Gln
                    355                 360                 365

Leu Ile Ile Ser Thr Val Ile Met Thr Val Gly Ile Ala Ile Val Ser
                    370                 375                 380

Trp Val Gly Leu Pro Thr Ser Phe Thr Ile Phe Asn Phe Gly Thr Gln
        385                 390                 395                 400

Lys Val Val Lys Asn Trp Gln Leu Phe Leu Cys Val Cys Val Gly Leu
                        405                 410                 415

Trp Ala Gly Leu Ile Ile Gly Phe Val Thr Glu Tyr Tyr Thr Ser Asn
                        420                 425                 430

Ala Tyr Ser Pro Val Gln Asp Val Ala Asp Ser Cys Arg Thr Gly Ala
                    435                 440                 445

Ala Thr Asn Val Ile Phe Gly Leu Ala Leu Gly Tyr Lys Ser Val Ile
                    450                 455                 460

Ile Pro Ile Phe Ala Ile Ala Ile Ser Ile Phe Val Ser Phe Ser Phe
        465                 470                 475                 480

Ala Ala Met Tyr Gly Val Ala Val Ala Ala Leu Gly Met Leu Ser Thr
                        485                 490                 495

Ile Ala Thr Gly Leu Ala Ile Asp Ala Tyr Gly Pro Ile Ser Asp Asn
                        500                 505                 510

Ala Gly Gly Ile Ala Glu Met Ala Gly Met Ser His Arg Ile Arg Glu
                    515                 520                 525

Arg Thr Asp Ala Leu Asp Ala Ala Gly Asn Thr Thr Ala Ala Ile Gly
                    530                 535                 540

Lys Gly Phe Ala Ile Gly Ser Ala Ala Leu Val Ser Leu Ala Leu Phe
        545                 550                 555                 560

Gly Ala Phe Val Ser Arg Ala Gly Ile His Thr Val Asp Val Leu Thr
                        565                 570                 575

Pro Lys Val Ile Ile Gly Leu Leu Val Gly Ala Met Leu Pro Tyr Trp
                        580                 585                 590

Phe Ser Ala Met Thr Met Lys Ser Val Gly Ser Ala Ala Leu Lys Met
                    595                 600                 605

Val Glu Glu Val Arg Arg Gln Phe Asn Thr Ile Pro Gly Leu Met Glu
                    610                 615                 620

Gly Thr Ala Lys Pro Asp Tyr Ala Thr Cys Val Lys Ile Ser Thr Asp
        625                 630                 635                 640

Ala Ser Ile Lys Glu Met Ile Pro Pro Gly Cys Leu Val Met Leu Thr
                        645                 650                 655
```

-continued

| | | | | | | | | | | | | |
|---|---|---|---|---|---|---|---|---|---|---|---|---|
| Pro | Leu | Ile | Val | Gly | Phe | Phe | Gly | Val | Glu | Thr | Leu | Ser | Gly | Val |
| | | | 660 | | | | 665 | | | | 670 | | | |
| Leu | Ala | Gly | Ser | Leu | Val | Ser | Gly | Val | Gln | Ile | Ala | Ile | Ser | Ala | Ser |
| | | 675 | | | | | 680 | | | | | 685 | | | |
| Asn | Thr | Gly | Gly | Ala | Trp | Asp | Asn | Ala | Lys | Lys | Tyr | Ile | Glu | Ala | Gly |
| | 690 | | | | | | 695 | | | | 700 | | | | |
| Val | Ser | Glu | His | Ala | Lys | Ser | Leu | Gly | Pro | Lys | Gly | Ser | Glu | Pro | His |
| 705 | | | | | 710 | | | | | 715 | | | | | 720 |
| Lys | Ala | Ala | Val | Ile | Gly | Asp | Thr | Ile | Gly | Asp | Pro | Leu | Lys | Asp | Thr |
| | | | | 725 | | | | | 730 | | | | | 735 | |
| Ser | Gly | Pro | Ser | Leu | Asn | Ile | Leu | Ile | Lys | Leu | Met | Ala | Val | Glu | Ser |
| | | | 740 | | | | | 745 | | | | | 750 | | |
| Leu | Val | Phe | Ala | Pro | Phe | Phe | Ala | Thr | His | Gly | Gly | Ile | Leu | Phe | Lys |
| | | 755 | | | | | | 760 | | | | | 765 | | |
| Tyr | Phe | | | | | | | | | | | | | | |
| | 770 | | | | | | | | | | | | | | |